(12) United States Patent
Horseman et al.

(10) Patent No.: US 10,824,132 B2
(45) Date of Patent: Nov. 3, 2020

(54) INTELLIGENT PERSONAL PROTECTIVE EQUIPMENT

(71) Applicant: Saudi Arabian Oil Company, Dhahran (SA)

(72) Inventors: Samantha J. Horseman, Dhahran (SA); Daniel (Mohammed) Al-Abdrabbuh, Al Khobar (SA); Yasser F. Alem, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 88 days.

(21) Appl. No.: 15/834,779

(22) Filed: Dec. 7, 2017

(65) Prior Publication Data

US 2019/0179286 A1    Jun. 13, 2019

(51) Int. Cl.
*G05B 9/02*        (2006.01)
*G05B 19/406*      (2006.01)
(Continued)

(52) U.S. Cl.
CPC ..... *G05B 19/406* (2013.01); *A41D 19/01594* (2013.01); *A41F 9/002* (2013.01);
(Continued)

(58) Field of Classification Search
CPC ... A41D 19/01594; A41F 9/002; A42B 3/046; A43B 3/0005; A43B 3/02;
(Continued)

(56) References Cited

U.S. PATENT DOCUMENTS 4,951,963 A    8/1990  Behr et al.
4,998,534 A    3/1991  Claxton, III et al.
(Continued)

FOREIGN PATENT DOCUMENTS

AU    767533 B2    11/2003
CN    101065752 A  10/2007
(Continued)

OTHER PUBLICATIONS

Electric double-layer capacitor Wikipedia; available at the website: http://en.wikipedia.org/wiki/electric_double-layer_capacitor as of Dec. 5, 2014; pp. 1-8.
(Continued)

*Primary Examiner* — Zhipeng Wang
(74) *Attorney, Agent, or Firm* — Bracewell LLP; Constance G. Rhebergen; Christopher L. Drymalla

(57) ABSTRACT

Provided are systems and methods for integrated control and safety systems (ICSSs) that employ intelligent personal protective equipment (PPE). In some embodiments, an industrial plant system includes an industrial safety system (ISS) for monitoring a safety status of an industrial plant and one or more intelligent PPE systems worn by personnel located in the industrial plant. Each of the intelligent PPE systems includes one or more intelligent PPE devices for sensing personal and environmental characteristics of a person wearing the intelligent PPE system, and transmits safety data corresponding to the personal and environmental characteristics sensed. The ISS collects the safety data, determines (based on the safety data) whether a safety incident has occurred and, in response to determining that a safety incident has occurred, executes a response to the safety incident.

20 Claims, 6 Drawing Sheets

(51) Int. Cl.
  *A42B 3/04*     (2006.01)
  *A41D 19/015*   (2006.01)
  *A43B 3/00*     (2006.01)
  *A43B 3/02*     (2006.01)
  *A61F 9/02*     (2006.01)
  *A61B 5/0476*   (2006.01)
  *G06Q 50/26*    (2012.01)
  *G06F 1/16*     (2006.01)
  *A41F 9/00*     (2006.01)
  *H04Q 9/00*     (2006.01)

(52) U.S. Cl.
  CPC ............ *A42B 3/046* (2013.01); *A43B 3/0005* (2013.01); *A43B 3/02* (2013.01); *A61B 5/0476* (2013.01); *A61F 9/029* (2013.01); *G06F 1/163* (2013.01); *G06Q 50/265* (2013.01); *H04Q 9/00* (2013.01); *A61B 2503/20* (2013.01); *G05B 2219/31439* (2013.01); *G05B 2219/50193* (2013.01)

(58) Field of Classification Search
  CPC ... A61B 2503/20; A61B 5/0476; A61F 9/029; G05B 19/406; G05B 2219/31439; G05B 2219/50193; G06F 1/163; G06Q 50/265; H04Q 9/00
  See application file for complete search history.

(56) References Cited

U.S. PATENT DOCUMENTS

| | | | |
|---|---|---|---|
| 5,000,188 A | 3/1991 | Kojima |
| 5,111,539 A | 5/1992 | Hiruta et al. |
| 5,253,656 A | 10/1993 | Rincoe et al. |
| 5,304,112 A | 4/1994 | Mrklas et al. |
| 5,305,238 A | 4/1994 | Starr, III |
| 5,323,650 A | 6/1994 | Fullen et al. |
| 5,331,549 A | 7/1994 | Crawford, Jr. |
| 5,343,869 A | 9/1994 | Pross et al. |
| 5,359,231 A | 10/1994 | Flowers et al. |
| 5,410,471 A | 4/1995 | Alyfuku et al. |
| 5,435,315 A | 7/1995 | McPhee et al. |
| 5,441,047 A | 8/1995 | David |
| 5,542,420 A | 8/1996 | Goldman et al. |
| 5,570,301 A | 10/1996 | Barrus |
| 5,573,269 A | 11/1996 | Gentry et al. |
| 5,626,145 A | 5/1997 | Clapp et al. |
| 5,673,691 A | 10/1997 | Abrams et al. |
| 5,722,418 A | 3/1998 | Bro |
| 5,792,047 A | 8/1998 | Coggins |
| 5,813,993 A | 9/1998 | Kaplan et al. |
| 5,926,806 A | 7/1999 | Marshall et al. |
| 5,937,387 A | 8/1999 | Summerell et al. |
| 6,033,344 A | 3/2000 | Trulaske et al. |
| 6,049,281 A | 4/2000 | Osterweil |
| 6,080,106 A | 6/2000 | Lloyd et al. |
| 6,083,156 A | 7/2000 | Lisiecki |
| 6,104,296 A | 8/2000 | Yasuchi et al. |
| 6,148,280 A | 11/2000 | Kramer |
| 6,149,586 A | 11/2000 | Elkind |
| 6,190,314 B1 | 2/2001 | Ark et al. |
| 6,198,394 B1 | 3/2001 | Jacobsen et al. |
| 6,203,495 B1 | 3/2001 | Bardy |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,345,839 B1 | 2/2002 | Kuboki et al. |
| 6,353,764 B2 | 3/2002 | Imagawa et al. |
| 6,369,337 B1 | 4/2002 | Machiyama |
| 6,381,577 B1 | 4/2002 | Brown |
| 6,383,136 B1 | 5/2002 | Jordan |
| 6,408,263 B1 | 6/2002 | Summers |
| 6,425,862 B1 | 7/2002 | Brown |
| 6,450,530 B1 | 9/2002 | Frasher et al. |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,594,607 B2 | 7/2003 | Lavery |
| 6,646,556 B1 | 11/2003 | Smith et al. |
| 6,648,820 B1 | 11/2003 | Sarel |
| 6,658,572 B1 | 12/2003 | Craig |
| 6,669,286 B2 | 12/2003 | Iusim |
| 6,673,027 B2 | 1/2004 | Fischer |
| 6,675,130 B2 | 1/2004 | Kanevsky et al. |
| 6,692,258 B1 | 2/2004 | Kurzweil |
| 6,705,990 B1 | 3/2004 | Gallant et al. |
| 6,736,642 B2 | 5/2004 | Bajer |
| 6,767,330 B2 | 7/2004 | Lavery et al. |
| 6,768,246 B2 | 7/2004 | Pelrine et al. |
| 6,781,067 B2 | 8/2004 | Montagnino et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,931,359 B2 | 8/2005 | Tamada |
| 6,982,497 B2 | 1/2006 | Rome |
| 7,005,757 B2 | 2/2006 | Pandian |
| 7,027,621 B1 | 4/2006 | Prokoski |
| 7,063,665 B2 | 6/2006 | Hasegawa et al. |
| 7,074,198 B2 | 7/2006 | Krullaards |
| 7,104,965 B1 | 9/2006 | Jiang et al. |
| 7,109,872 B2 | 9/2006 | Balaban et al. |
| 7,128,577 B2 | 10/2006 | Renaud |
| 7,152,024 B2 | 12/2006 | Marschner |
| 7,155,158 B1 | 12/2006 | Iuppa |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallenberger |
| 7,304,580 B2 | 12/2007 | Sullivan et al. |
| 7,315,249 B2 | 1/2008 | Littell |
| 7,351,206 B2 | 4/2008 | Suzuki |
| 7,399,276 B1 | 7/2008 | Brown et al. |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,717,866 B2 | 5/2010 | Damen |
| 7,771,318 B2 | 8/2010 | Narayanaswami |
| 7,830,249 B2 | 11/2010 | Dorneich et al. |
| 7,844,347 B2 | 11/2010 | Brabec |
| 7,849,115 B2 | 12/2010 | Reiner |
| 7,901,324 B2 | 3/2011 | Kodama |
| 7,958,002 B2 | 6/2011 | Bost |
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird |
| 8,024,202 B2 | 10/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,179,269 B2 | 5/2012 | Yanagi et al. |
| 8,180,457 B2 | 5/2012 | Matos |
| 8,200,323 B2 | 6/2012 | Dibenedetto et al. |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,428,962 B1 | 4/2013 | Brinkley et al. |

(56) References Cited

U.S. PATENT DOCUMENTS

| | | |
|---|---|---|
| 8,477,039 B2 | 7/2013 | Gleckler et al. |
| 8,487,456 B2 | 7/2013 | Donelan et al. |
| 8,597,121 B2 | 12/2013 | Andres Del Valle |
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer |
| 8,775,196 B2 | 7/2014 | Simpson et al. |
| 8,956,292 B2 | 2/2015 | Wekell et al. |
| 9,043,217 B2 | 5/2015 | Cashman et al. |
| 9,044,172 B2 | 6/2015 | Baxi et al. |
| 9,364,714 B2 | 6/2016 | Koduri et al. |
| 10,169,962 B1 * | 1/2019 | Walker .................. G08B 5/36 |
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0008625 A1 * | 1/2002 | Adams .............. G08B 21/0211 |
| | | 340/573.1 |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0214408 A1 | 11/2003 | Grajales et al. |
| 2003/0222440 A1 | 12/2003 | Basir |
| 2003/0226695 A1 | 12/2003 | Mault |
| 2004/0002634 A1 | 1/2004 | Nihtila |
| 2004/0004547 A1 * | 1/2004 | Appelt .................. G08B 21/02 |
| | | 340/573.1 |
| 2004/0015191 A1 | 1/2004 | Otman |
| 2004/0095378 A1 | 5/2004 | Vigue |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0060217 A1 | 3/2005 | Douglas et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0090135 A1 | 4/2006 | Fukuda |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0232937 A1 | 10/2007 | Lam et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0015422 A1 | 6/2008 | Wessel |
| 2008/0140140 A1 | 6/2008 | Grimley |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Ouwerkerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0205693 A1 * | 8/2008 | Kitamura .......... G05B 23/0267 |
| | | 382/100 |
| 2008/0218331 A1 | 9/2008 | Baillot |
| 2008/0228046 A1 | 9/2008 | Fatatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |

(56) References Cited

U.S. PATENT DOCUMENTS

| | | |
|---|---|---|
| 2008/0258921 A1 | 10/2008 | Woo et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Fu et al. |
| 2010/0312606 A1 | 12/2010 | Gala |
| 2010/0332250 A1 | 12/2010 | Simpson |
| 2011/0030838 A1* | 2/2011 | Turiello .............. A62B 7/02 141/1 |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0270135 A1 | 11/2011 | Dooley et al. |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Hotary et al. |
| 2012/0117020 A1 | 5/2012 | Davis |
| 2012/0122430 A1 | 5/2012 | Hutchings et al. |
| 2012/0127157 A1 | 5/2012 | Adler |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1* | 1/2013 | Horseman .......... G06F 19/3418 705/2 |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0217350 A1* | 8/2013 | Singh .................. H04B 1/06 455/130 |
| 2013/0226413 A1 | 8/2013 | Cuddihy et al. |
| 2013/0234826 A1 | 9/2013 | Sekiguchi et al. |
| 2013/0243208 A1 | 9/2013 | Fawer |
| 2013/0281798 A1 | 10/2013 | Rau et al. |
| 2013/0282609 A1* | 10/2013 | Au .................. G06K 9/6211 705/325 |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2013/0308099 A1 | 11/2013 | Stack |
| 2013/0331993 A1 | 12/2013 | Detsch et al. |
| 2013/0334851 A1 | 12/2013 | Hoell et al. |
| 2014/0041105 A1* | 2/2014 | Zemlak .............. A61F 9/029 2/426 |
| 2014/0067001 A1 | 3/2014 | Schwibner et al. |
| 2014/0100464 A1 | 4/2014 | Kaleal et al. |
| 2014/0107718 A1 | 4/2014 | Foote |
| 2014/0129401 A1 | 5/2014 | Kruz et al. |
| 2014/0156259 A1 | 6/2014 | Dolan et al. |
| 2014/0172461 A1 | 6/2014 | Rogers |

(56) References Cited

U.S. PATENT DOCUMENTS

| | | |
|---|---|---|
| 2014/0222095 A1 | 8/2014 | Einy |
| 2014/0304020 A1 | 10/2014 | Casper |
| 2014/0317914 A1 | 10/2014 | Shaker |
| 2014/0372133 A1 | 12/2014 | Austrum et al. |
| 2015/0025928 A1 | 1/2015 | Kang et al. |
| 2015/0050623 A1 | 2/2015 | Falash et al. |
| 2015/0134347 A1 | 5/2015 | Faurie et al. |
| 2015/0199494 A1 | 7/2015 | Koduri et al. |
| 2015/0222096 A1 | 8/2015 | Nakayama |
| 2015/0338265 A1 | 11/2015 | Carreel et al. |
| 2015/0375028 A1 | 12/2015 | Oteman et al. |
| 2016/0132046 A1* | 5/2016 | Beoughter ......... G05B 19/4184 700/17 |
| 2016/0321935 A1 | 11/2016 | Mohler et al. |
| 2017/0245806 A1* | 8/2017 | Elhawary ............ G06F 19/3481 |
| 2017/0270481 A1* | 9/2017 | Morgenthau ...... H04W 72/0453 |
| 2017/0290516 A1 | 10/2017 | Nguyen et al. |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |
| EP | 1407713 B1 | 9/2008 |
| EP | 2151355 A1 | 2/2010 |
| EP | 2248461 A2 | 11/2010 |
| EP | 2924674 A1 | 9/2015 |
| JP | 05-049603 A | 3/1993 |
| JP | H07204168 A | 8/1995 |
| JP | H10283150 A | 10/1998 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001236141 A | 8/2001 |
| JP | 2001356849 A | 12/2001 |
| JP | 2002065630 A | 3/2002 |
| JP | 2002109061 A | 4/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003091598 A | 8/2003 |
| JP | 2003235813 A | 8/2003 |
| JP | 2003247991 A | 9/2003 |
| JP | 2003256578 A | 9/2003 |
| JP | 2003525676 A | 9/2003 |
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2006239157 A | 9/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010267267 A | 11/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 2001028416 A1 | 4/2001 |
| WO | 2001086403 A2 | 11/2001 |
| WO | 03077110 A2 | 9/2003 |
| WO | 2005064447 A2 | 7/2005 |
| WO | 2006022465 A2 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | 2013006627 A1 | 1/2013 |
| WO | 2013006642 A2 | 1/2013 |
| WO | 2013006644 A1 | 1/2013 |
| WO | 2014023422 A1 | 2/2014 |

OTHER PUBLICATIONS

Elliott, Stephen N., et al. "Cognitive load theory: Instruction-based research with applications for designing tests." Proceedings of the National Association of School Psychologists' Annual Convention, Boston, MA, February. vol. 24. 2009.

EPO: "Notice from the European Patent Office dated Oct. 1, 2007 concerning business methods" Official Journal EPO, vol. 30, No. 11, Nov. 1, 2007, pp. 592-593, XP007905525.

Fadel, Charles, et al. "Multimodal Learning Through Media: What the Research Says" Cisco Systems, Inc. (2008) pp. 1-24.

Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.

Filmer, Hannah L., et al. "Disrupting prefrontal cortex prevents performance gains from sensory-motor training." The Journal of Neuroscience 33.47 (2013): 18654-18660.

Fougnie, Daryl, and René Marois. "What limits working memory capacity? Evidence for modality-specific sources to the simultaneous storage of visual and auditory arrays." Journal of Experimental Psychology: Learning, Memory, and Cognition 37.6 (2011): 132.

Georgia Tech, "Prowess Proactive Wellness Environment Support System", Dec. 12, 2009, pp. 1-27, www.hsi.gatech.edu/onsitecenter/index.php/PROWESS.

Goetzel et al. "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.

Goetzel et al. 'Estimating the Return-on-Investment From Changes in Employee Health Risks on TheDow Chemical Company's Health Care Costs'—J Occup Environ Med. (JOEM) vol. 47, No. 8, dated Aug. 2005; pp. 759-768.

Goetzel et al. 'Health, Absence, Disability, and Presenteeism Cost Estimates of Certain Physical and MentalHealth Conditions Affecting U.S. Employers'—J Occup Environ Med. (JOEM) vol. 46, No. 4, dated Apr. 2004; pp. 398-412.

Goetzel et al. 'Second-Year Results of an Obesity Prevention Program at TheDow Chemical Company'—J Occup Environ Med. (JOEM) vol. 52, No. 3, dated Mar. 2010; pp. 291-302.

Goetzel et al. 'The Health and Productivity Cost Burden of the "Top 10" Physical and Mental HealthConditions Affecting Six Large U.S. Employers in 1999'—J Occup Environ Med. (JOEM) vol. 45, No. 1, dated Jan. 2003; pp. 5-14.

Goetzel et al. 'The Long-Term Impact of Johnson & Johnson's Health & Wellness Program onEmployee Health Risks'—J Occup Environ Med. (JOEM) vol. 44, No. 5, dated May 2002; pp. 417-424.

Goetzel et al. 'The Workforce Wellness Index'—J Occup Environ Med. (JOEM) vol. 55, No. 3, dated Mar. 2013; pp. 272-279.

(56) References Cited

OTHER PUBLICATIONS

Goetzel et al. The Predictive Validity of the HERO Scorecard in Determining Future Health Care Cost and Risk Trends—J Occup Environ Med. (JOEM) vol. 56, No. 2, dated Feb. 2014; pp. 136-144.
Hacker, et al. "Representation and visualization of variability in a 3D anatomical atlas using the kidney as an example." Medical Imaging. International Society for Optics and Photonics, 2006. XP055342027 (pp. 1-7).
Health/Medical Writers eHealthcareWorld 2000. (May 1). MyDailyHealth.com (pp. 1-3).
Hemp, P., "Presenteeism: At Work—But Out of It", Harvard Business Review, Oct. 2004, pp. 49-58.
Hill, Jr., Randall W.; "How Virtual Humans Can Build Better Leaders" Harvard Business Review Jul. 25, 2014; pp. 1-4.
Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.
Horseman, Samantha, et al.; "Gamefication of Health, Safety and the Environment {HSE): An Avatarial Solution" American Society of Safety Engineers 11th Professional Development Conference & Exhibition, Bahrain, Mar. 2014;pp. 1-10.
Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012. (pp. 1-5).
International Preliminary Report on Patentability for International Application No. PCT/US2012/045395, dated Jan. 7, 2014. (pp. 1-12).
International Preliminary Report on Patentability for International Application No. PCT/US2012/045401 dated Jan. 7, 2014. (pp. 1-9).
International Preliminary Report on Patentability for International Application No. PCT/US2012/045407 dated Jan. 7, 2014. (pp. 1-8).
International Preliminary Report on Patentability for International Application No. PCT/US2012/045410 dated Jan. 7, 2014 (pp. 1-8).
International Preliminary Report on Patentability for International Application No. PCT/US2012/045414 dated Jan. 7, 2014 (pp. 1-8).
International Preliminary Report on Patentability for International Application No. PCT/US2012/045419 dated Jan. 7, 2014 (pp. 1-11).
International Preliminary Report on Patentability for International Application No. PCT/US2012/045427 dated Jan. 7, 2014 (pp. 1-10).
International Preliminary Report on Patentability for International Application No. PCT/US2012/045435 dated Jan. 7, 2014 (pp. 1-10).
International Preliminary Report on Patentability for International Application No. PCT/US2012/045442 dated Jan. 7, 2014 (pp. 1-10).
International Preliminary Report on Patentability for International Application No. PCT/US2012/045447 dated Jan. 7, 2014 (pp. 1-8).
International Preliminary Report on Patentability for International Application No. PCT/US2012/045452 dated Jan. 7, 2014 (pp. 1-9).
International Search Report & Written Opinion for International Application No. PCT/US2012/045401, dated Feb. 5, 2013. (pp. 1-13).
International Search Report & Written Opinion for International Application No. PCT/US2012/045407, dated Jan. 23, 2013. (pp. 1-15).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045447, dated Jan. 18, 2013. (pp. 1-12).
International Search Report and Written Opinion for International Application No. PCT/US2004/045442, dated Nov. 7, 2012, pp. 1-14.
International Search Report and Written Opinion for International Application No. PCT/US2012/045395, dated Dec. 3, 2012, pp. 1-16.
International Search Report and Written Opinion for International Application No. PCT/US2012/045419, dated Dec. 6, 2012, pp. 1-16.
International Search Report and Written Opinion for International Application No. PCT/US2012/045427, dated Dec. 3, 2012, pp. 1-14.
International Search Report and Written Opinion for International Application No. PCT/US2012/045452, dated Dec. 3, 2012, pp. 1-14.
International Search Report and Written Opinion for International Application No. PCT/US2016/064518; International Filing Date Dec. 21, 2016; Report dated Feb. 17, 2017; (pp. 1-16).
International Search Report and Written Opinion for International Application No. PCT/US2016/065042; International Filing Date Dec. 6, 2016; Report dated Mar. 17, 2017; pp. 1-15.
International Search Report and Written Opinion for International Application No. PCT/US2016/064520; International Filing Date Dec. 2, 2016; Report dated Mar. 27, 2017; pp. 1-10.
International Search Report and Written Opinion for International PCT application PCT/US2016/064521; International Filing Date Dec. 2, 2016; Report dated Mar. 20, 2017; pp. 1-17.
International Search Report and Written Opinion for related PCT application PCT/US2018/064161 dated Feb. 28, 2019; pp. 1-13.
"40 Best Companies for Leaders—2014" Chief Executive, available as of Dec. 13, 2015 at the website: http://chiefexecutive.net/40-best-companies-for-leaders-2014/; pp. 1-3.
"Augmented Reality", retrieved from <http://en.wikipedia.org/wiki/Augmented_reality>, May 30, 2012. pp. 1-18.
"Biofeedback—MayoClinic.com", retrieved from <http://www.mayoclinic.com/health/biofeedback/MY01072>, May 7, 2012. (pp. 1-2).
"Cardinus Risk Management | Ergonomic & DSE Risk Assessments", retrieved from <http://www.cardinus.com/>, Sep. 12, 2012. (pp. 1-2).
"Chronic diseases and health promotion" Centers for Disease Control and Prevention, 2011, <http://www.cdc.gov/chronicdisease/overview> [Accessed Feb. 2, 2011].
"Clever toilet checks on your health", retrieved from <http://articles.cnn.com/2005-06-28/techispark.toilet_1_toilet-toto-bathroom?_s=PM:TECH>, Jun. 28, 2005. (pp. 1-2).
"Electroencephalography (EEG)", retrieved from <http://www.emedicinehealth.com/script/main/art.asp? articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).
"EmotivEPOC Software Devlopment Kit", retrieved from <www.emotiv.com/store/hardware/epoc-bci-eeg/developer-neuroheadset/>, Jun. 11, 2012. (pp. 1-2).
"Kinect—Xbox.com", retrieved from <http://www.xbox.com/en-US/kinect>, Jun. 11, 2012. (pp. 1-3).
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Murray Hill, WellMed Team to Offer Next Generation Online Preventive Health Services" ProQuest, PR Newswire, New York, Nov. 3, 1999, 3 pages.
"National Health Expenditure Data", Centers for Medicare & Medicaid Services, available at: <https://www.cms.gov/Research-Statistics-Data-and-Systems/Statistics-Trends-and-Reports/NationalHealthExpendData/index.html>, accessed Nov. 18, 2013, pp. 1-2.
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).

(56) References Cited

OTHER PUBLICATIONS

"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"Research programs—Philips Research", retrieved from <http://www.research.philips.com/programs/index.html>, May 7, 2012. (pp. 1-2).
"RJL Systems, Products", retrieved from <http://www.rjlsystems.com/products.shtml>, May 7, 2012. (p. 1).
"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
Rosen, Yigal. "The effects of an animation-based on-line learning environment on transfer of knowledge and on motivation for science and technology learning." Journal of Educational Computing Research 40.4 (2009): 451-467.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Simmonds, Bethany, et al. "Objectively assessed physical activity and subsequent health service use of UK adults aged 70 and over: A four to five year follow up study." PloS one 9.5 (2014): e97676.
Slater et al., "Taking Steps: The Influence of a Walking Technique on Presence in Virtual Reality", ACM Transactions on Computer-Human Interaction, Sep. 1995, pp. 201-219, vol. 2 No. 3.
Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the web.
Stephens: "I am 38. My heart is only 33, but my lungs are aged 52. Why?" Mail Online; http://www.dailymail.co.uk/health/article-1249009/I-38-My-heart-only33-lungs-aged-52-Why.html; retrieved on Feb. 3, 2017; XP055342045 (pp. 1-7).
Sullivan 'Making the Business Case for Health and Productivity Management'—J Occup Environ Med. (JOEM) vol. 46, No. 6 suppl, dated Jun. 2004; pp. S56-S61.

The American Heritage Dictionary of the English Language, definition of planar, 2000.
The constitution of the World Health Organization, World Health Organization, WHO Chronicle, 1947, pp. 1-202.
Veeva Systems and Zinc Ahead Join Forces available as of Oct. 2, 2015 at the website: http://www.veeva.com; pp. 1-6.
Wang, Xiaoning. "An Empirical Study of Optimizing Cognitive Load in Multimedia Integrated English Teaching." Studies in Literature and Language 9.3 (2014): 70.
Withings, The Internet connected Body Scale, retrieved with the Wayback Machine using link at www.withings.com, Jan. 11, 2010.
World Economic Forum 'The Workplace Wellness Alliance—Making the Right Investment: Employee Health and the Power of Metrics' dated Jan. 2013; pp. 1-35.
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo In Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, 1 page, XP002456414.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Agarabi, Mina, et al., "A sEMG-based Method for Assessing the Design of Computer Mice" 26th Annual International Conference of the IEEE EMBS, Sep. 1-5, 2004; pp. 2450-2453.
Aldana, S., "Financial Impact of health promotion programs: a comprehensive review of the literature", American Journal of Health Promotion,155, 2001, pp. 296-320.
Aldana, S., Merrill, R., Price, K., Hardy, A., and Hager, R., "Financial impact of a comprehensive multi-site worksite health promotion program", Preventive Medicine, 40, Jul. 2004, pp. 131-137.
Alfredo Vazquez Carazo, "Novel Piezoelectric Transducers for High Voltage Measurements", Jan. 2000, pp. 1-277.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Asplund, Christopher L., et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 25.3 (2014): 824-831.
Baicker, K., Cutler, D., Song, Z., "Worksite wellness programs can generate savings", Health Affairs 29(2), Jan. 2010, pp. 1-8.
Bed-Check Co., Bed-Check Monitoring Systems, 2006.
Berger et al. 'Investing in Healthy Human Capital'—J Occup Environ Med. (JOEM) vol. 45, No. 12, dated Dec. 2003; pp. 1213-1225.
Berry, Leonard et al., "What's the Hard Return on Employee Wellness Programs?", Harvard Business Review, Dec. 2010. (pp. 1-10).
Borah, J. "Conceptual modeling—The missing link of simulation development." Proceedings of the 2002 Spring Simulation Conference. 2002. AEgis Technologies Group; pp. 1-7.

(56) References Cited

OTHER PUBLICATIONS

Brown et al, "Prowess Proactive Wellness Environment Support System", Dec. 10, 2009, pp. 1-19, www.hsi.gatech.edu/onsitecenter/index.php/PROWESS.

Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.

Campbell et al., "The Rise of People-Centric Sensing", IEEE Computer Society, 2008, pp. 12-21, IEEE.

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Chapman, Larry S. MPH, "Meta-evaluation of Worksite Health Promotion Economic Return Studies: 2005 Update", Jul./Aug. 2005. (pp. 1-11).

Collins English Dictionary, definition of mat, 2008, retrieved at www.collinsdictionary.com.

Duke, Sean, "A 'smartphone' based defibrillator" Science Spin, Jan. 11, 2011: pp. 1-2.

Dux, Paul E., and René Marois. "The attentional blink: A review of data and theory." Attention, Perception, & Psychophysics 71.8 (2009): 1683-1700.

Dux, Paul E., et al. "Training improves multitasking performance by increasing the speed of information processing in human prefrontal cortex." Neuron 63.1 (2009): 127-138.

Edington, D. W., "Emerging research: a view from one research centre", American Journal of Health Promotion, 15(5), May/Jun. 2001, pp. 341-349.

Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.

International Search Report and Written Opinion for PCT/US2014/056427 dated Apr. 22, 2015.

International Search Report and Written Opinion for PCT/US2014/069498 dated Apr. 1, 2015.

Ivanoff, Jason, Philip Branning, and René Marois. "fMRI evidence for a dual process account of the speed-accuracy tradeoff in decision-making." PLoS one 3.7 (2008): e2635. pp. 1-14.

Jamison, Dean T., et al.; "The World Health Report 1999" World Health Organization, WHO Library Cataloguing in Publication Data, 1999; pp. 1-136.

Johns, G., "Presenteeism in the Workplace: A review and research agenda", Journal of Organizational Behavior, Jul. 31, 2009, pp. 519-542.

Kelly et al. The Novartis Health Index: A Method for Valuing the Economic Impact of Risk Reduction in a Workforce—J Occup Environ Med. (JOEM) vol. 52, No. 5, dated May 2010; pp. 528-535.

Knikou, Maria. "The H-reflex as a probe: pathways and pitfalls." Journal of neuroscience methods 171.1 (2008): 1-12.

Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.

Kymissis et al. "Parasitic Power Harvesting in Shoes" Digest of Papers, Second International Symposium on Wearable Computers, Pittsburgh, PA, Oct. 19-20, 1998, pp. 132-139, XP032385438.

Lamkin, Paul; "The best VR headsets: Oculust Rift, PlayStation VR, GEAR VR, HTC Vive . . . virtual reality is back baby" 10 Sep. 16, 2015; available as of Oct. 21, 2015 at the website: http://www.wearable.com/headgear/the-best-ar-and-vrheadsets;pp. 1-1.

Marois, René, and Jason Ivanoff. "Capacity limits of information processing in the brain." Trends in cognitive sciences 9.6 (2005): 296-305.

Moreno, Roxana, and Alfred Valdez. "Cognitive load and learning effects of having students organize pictures and words in multimedia environments: The role of student interactivity and feedback." Educational Technology Research and Development 53.3 (2005).

Moreno, Roxana, and Richard Mayer. "Interactive multimodal learning environments." Educational Psychology Review 19.3 (2007): 309-326.

Moreno, Roxana. "Learning in high-tech and multimedia environments." Current directions in psychological science 15.2 (2006): 63-67.

Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.

Nintendo of America Inc., Wii Balance Board Operations Manual, 2008, pp. 1-10.

Nintendo of America Inc., Wii Fit Instruction Booklet, 2008, pp. 1-28.

Nintendo Wii Fit, https://www.youtube.com/watch?v=-Taruqvk30E, May 11, 2008.

Ovans, Andrea; What Resilience Means, and Why it Matters Harvard Business Review Jan. 5, 2015; pp. 1-6.

Priya, S., "Advances in Energy Harvesting Using Low Profile Piezoelectric Transducers", Materials Science & Engineering, Springer, Mar. 2007, pp. 165-182.

Prochaska et al. 'The Well-Being Assessment for Productivity'—J Occup Environ Med. (JOEM) vol. 53, No. 7, dated Jul. 2011; pp. 735-768.

Qlik Technology Partners available as of Oct. 21, 2015 at the website: http://www.qlik.com/us/partners/technologypartners;pp. 1-21.

Quick, James Campbell, et al. "Executive health: Building strength, managing risks" Academy of Management Executive, May 2000, vol. 14, No. 2, pp. 33-45.

Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.

Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.

Ready, Douglas A., et al.; "Are You a High Potential?" Harvard Business Review Jun. 2010; pp. 1-13.

Reidel, J.E., Baase, C., "The effect of disease prevention & health promotion on worksite productivity: a literature review", American Journal of Health Promotion, 15:3, Jan./Feb. 2001, pp. 167-191, 243.

Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.

Robertini, Nadia, et al., "Capture of Arm-Muscle Deformations using a Depth-Camera" 10 European Conference on Visual Media Production, London, UK, Nov. 6-7, 2013; pp. 1-10.

Roberts, R.O.,Bergstralh, E.J., Schmidt, L, Jacobsoen,S.J., "Comparison of Self Reported and Medical Record Health Care Utilization Measures", Journal of Clinical Epidemiology, 49:9, Feb. 1996, pp. 989-995.

\* cited by examiner

INTELLIGENT PERSONAL PROTECTIVE EQUIPMENT

FIELD

Embodiments relate generally to safety monitoring and more particularly to industrial safety systems employing intelligent personal protective equipment (PPE).

BACKGROUND

Employee health and safety continues to be an area of great importance to employers. Many companies are committed to surrounding employees with a safe working environment to prevent workplace accidents that may otherwise occur. Safety concerns are especially heightened for industrial worksites (often referred to as "industrial plants" or "plants"). Industrial plants include, for example, oil and gas plants, nuclear plants, power plants, and the like. Industrial plants are typically complex systems that include large machinery, electrical systems, flow control systems, or the like. Large machinery can include, for example, turbomachinery, such as turbines, generators and compressors with components rotating at an extremely high rates. Electrical systems can include, for example, power systems that generate and transport high-voltage electrical power. Flow control systems can include, for example, flow control mechanisms, such as valves, pressure vessels and pipes that regulate the flow of high pressure fluids and gas, such as oil and natural gas. Given the complexity of the systems employed, industrial plant systems typically require special attention to safety to minimize the risk of safety incidents, such as physical injuries to persons, damage to the industrial plant systems themselves, and injuries to the environment.

Industrial plants often employ a process control system (PCS) and an industrial safety system (ISS). These systems are normally integrated with one another and are referred to collectively as an integrated control and safety system (ICSS). The PCS typically controls the various processes of industrial plant. For example, a PCS may monitor and control the operations of an industrial plant's systems to provide for the day-to-day operations of the industrial plant, such as the processing of oil and gas. The ISS can include an additional layer of monitoring and control that protects persons, the industrial plant systems and the environment. An ISS may employ safety sensors and controllers that monitor the safety status of the industrial plant and, if needed, initiates action to ensure that any potential and actual safety issues are addressed. As an example, if an ISS detects an exceedingly high pressure within a pressure vessel, the ISS may command the PCS to close an emergency shutdown (ESD) valve (to terminate a fluid supply to the pressure vessel) and command the PCS to open a pressure safety valve (PSV) (to relive pressure in the pressure vessel) to prevent rupturing of the pressure vessel. Industrial safety system can take various forms, such as process safety (or shutdown) systems (PSS) and safety shutdown system (SSS), such as emergency shutdown (ESD) and emergency depressurization-(EDP) systems.

SUMMARY

Applicants have recognized that existing industrial safety systems (ISSs) generally rely on sensing and reacting to physical phenomena, such as measurements of temperature, pressure, flow rate and the like. Although these system can be effective at anticipating and preventing accidents that manifest by way of such physical phenomena, they may not detect or prevent other accidents and near accidents (or "near misses"). For example, existing ISSs may provide an effective means to detect and prevent critical and catastrophic safety events, such as an explosions caused by a high pressure condition; however, existing ISSs may not be effective at detecting and preventing less critical and less catastrophic safety events, such a physical actions of employees that lead to physical injuries, or employee conditions, such as the onset of physical fatigue, that could lead to an accident. Applicants have further recognized that many of these "other" accidents and near misses happen at a relatively high frequency, and although they may not be as individually detrimental as certain catastrophic safety events, taken as a whole, these other accidents and near misses can have a significant impact on industrial plant safety and the wellbeing of employees. For example, a large number of separate injuries caused by physical overexertion of individual employees can have a similar or greater impact than a single critical and catastrophic safety event. Moreover, the detection and prevention of near misses can enhance industrial plant safety by helping to identify and remedy the source of safety events, large and small, before they occur.

Recognizing these and other shortcomings of existing ISSs, Applicants have developed an integrated control and safety system (ICSS) that employs intelligent personal protective equipment (PPE). In some embodiments, sensing devices of an ISS are integrated with PPE that is worn by employees during the course of their work duties. PPE can include safety equipment, such as safety helmets, gloves, safety glasses, shoes, belts and the like that are worn by employees during the course working at an industrial plant. In many instances, persons are mandated to wear these and other types of PPE while in the industrial plant environment. In some embodiments, the sensing devices integrated in an intelligent PPE system worn by a person are employed to collect safety data for the person, including personal health data and/or environmental data.

The personal health data may include biometric health data for the person, such as heart rate, body temperature, brain activity, stress level, physical exertion, blink rate, heart rate, sweat rate, body position and/or the like. The environmental data may include data regarding the environment surrounding the person, such as a geographic location of the person, a temperature at the location of the person, and information for devices proximate to the location of the person. The information for devices proximate to the location of the person can include, for example, information regarding the status, configuration, and operation of devices within communication range of the intelligent PPE. In some embodiments, the personal health data is collected via safety sensors integrated into the PPE or otherwise worn by the person, such as heart rate sensors, body temperature sensors, electroencephalography (EEG) sensors, galvanic skin response (GSR) sensors, pressure sensors, image sensors, and position sensors. In some embodiments, the environmental data is collected via environmental safety sensors integrated into the PPE or otherwise worn by the person, such as temperature sensors, location sensors and communication devices. The communication devices may enable the PPE to communicate with other devices proximate to the location and/or to communicate with an ISS via a network of the ICSS.

In some embodiments, an intelligent PPE device includes intelligent headwear. For example, an intelligent PPE device can include a safety helmet (or "hard-hat") that includes temperature sensors, EEG sensors, position sensors, location sensors, and/or a wireless communication device integrated therein. In some embodiments, an intelligent PPE device includes intelligent hand wear. For example, an intelligent PPE device can include safety gloves that include temperature sensors, pressure sensors, GSR sensors, heart rates sensors, position sensors, a location sensor, and a wireless communication device integrated therein. In some embodiments, an intelligent PPE device includes intelligent footwear. For example, an intelligent PPE device can include safety boots that include temperature sensors, pressure sensors, position sensors, location sensors, and wireless communication devices integrated therein. In some embodiments, intelligent PPE includes intelligent eyewear. For example, an intelligent PPE device can include safety glasses that include image sensors, temperature sensors, position sensors, a location sensor, and a wireless communication device integrated therein. In some embodiments, an intelligent PPE device includes an intelligent article of clothing. For example, an intelligent PPE device can include a safety belt that includes temperature sensors, position sensors, a location sensor, and a wireless communication device integrated therein. Although certain examples are provided for the purpose of explanation, embodiments can include various combinations of PPE devices and integrated sensors.

In some embodiments, safety data for one or more persons in an industrial plant is collected from intelligent PPEs worn by the one or more persons, and various plant safety operations are undertaken based on the safety data collected. For example, if a critical safety incident (or "safety event") for a particular portion of the industrial plant is determined from the safety data collected, the ICSS may take steps to shut down operations in that portion of the plant and provide corresponding alerts. In some embodiments, the ICSS for an industrial plant can include several different layers of control and monitoring, and different levels of response can be instituted based on the level of a safety incident. For example, the ICSS can provide feedback to systems for a control room, a superintendent, a safety team, managers and employees that all interact to provide for operation of an ICSS. In the event of a relatively low-level safety incident for a person, the ICSS may provide direct feedback to the person. For example, if the ICSS detects five instances of an employee engaging in poor posture, the ICSS may send a message to the employee. In the event of a relatively high-level safety incident, the ICSS may provide feedback to various portions of the ICSS, and may effectuate an action to remedy the incident. For example, if the ICSS detects a health crisis for a person, such as an elevated heart rate for an extended duration, the ICSS may notify the control room, the superintendent, the safety team, and the person's manager, and may initiate suspension of operations that rely on that person and that could further jeopardize the health of that person, such suspend the operation of machinery under control of the person and/or located near the person.

Further, the integration of industrial internet of things (IIoT) may allow smart devices mounted on plant devices, such as smart sensors mounted on valves, to communicate directly with intelligent PPE devices, such as electroencephalography (EEG) devices in a safety helmet intelligent headwear PPE device. Such a configuration may enable smart devices to wirelessly communicate relevant plant information, such as signals indicative various plant operations and conditions (e.g., inefficiencies in pipeline flow rates, alerts of required maintenance, and corrosion), directly to persons in the plant environment or the ICSS. Such an incorporation of advanced human-machine interface may enhance real-time monitoring and output of the industrial plant.

Provided in some embodiments is an industrial plant system, including: an industrial safety system (ISS) adapted to monitor a safety status of an industrial plant, and one or more intelligent personal protective equipment (PPE) systems adapted to be worn by personnel located in the industrial plant. Each of the intelligent PPE systems includes one or more intelligent PPE devices adapted to sense personal and environmental characteristics of a person wearing the intelligent PPE system. Each of the intelligent PPE systems is adapted to transmit, to the industrial safety system, safety data corresponding to the personal and environmental characteristics of the person wearing the intelligent PPE system, sensed by the one or more intelligent PPE devices of the intelligent PPE system. The ISS is adapted to perform the following: collect, from the one or more intelligent PPE systems, the safety data; determine, based on the safety data collected, whether a safety incident has occurred; and in response to determining that a safety incident has occurred, execute a response to the safety incident.

In some embodiments, the one or more intelligent PPE devices include one or more of an intelligent headwear PPE device, an intelligent hand wear PPE device, an intelligent footwear PPE device, an intelligent eyewear PPE device, and an intelligent clothing device. In certain embodiments, the intelligent headwear PPE device includes an intelligent safety helmet, the intelligent hand wear PPE device includes intelligent safety gloves, the intelligent footwear PPE device includes intelligent safety boots, the intelligent eyewear PPE device includes intelligent safety glasses, or the intelligent clothing PPE device includes an intelligent safety belt. In some embodiments, the safety incident includes a critical safety incident, and the response to the safety incident includes suspending operations of the industrial plant and alerting entities of the industrial plant system. In certain embodiments, the safety incident includes a moderate safety incident, and the response to the safety incident includes alerting entities of the industrial plant system. In some embodiments, the system includes a smart device coupled to a plant device, adapted to transmit, to an intelligent PPE system worn by a person located in the industrial plant, environmental data indicative of a characteristic of the plant device. The intelligent PPE system including an EEG sensor and adapted to communicate the environmental data indicative of the characteristic of the plant device to the person by way of the EEG sensor.

Provided in some embodiments is a method of operating an industrial plant that includes the following: sensing, by one or more one or more intelligent personal protective equipment (PPE) systems worn by personnel located in an industrial plant, personal and environmental characteristics of the personnel, where each of the one or more intelligent PPE systems are worn by a person located in the industrial plant, where each of the intelligent PPE systems includes one or more intelligent PPE devices sensing personal and environmental characteristics of the person wearing the intelligent PPE system, and where the personal and environmental characteristics of the personnel include the personal and environmental characteristics sensed by the one or more intelligent PPE devices of the one or more intelligent PPE systems; transmitting, by the one or more PPE systems, safety data corresponding to the personal and environmental characteristics of the personnel; monitoring, by an industrial safety system (ISS), a safety status of the industrial plant, including: collecting, from the one or more intelligent PPE systems, the safety data; determining, based on the safety data collected, whether a safety incident has occurred; and in response to determining that a safety incident has occurred, executing a response to the safety incident.

In some embodiments, the one or more intelligent PPE devices include one or more of the following: an intelligent headwear PPE device, an intelligent hand wear PPE device, an intelligent footwear PPE device, an intelligent eyewear PPE device, and an intelligent clothing device. In certain embodiments, the intelligent headwear PPE device includes an intelligent safety helmet, the intelligent hand wear PPE device includes intelligent safety gloves, the intelligent footwear PPE device includes intelligent safety boots, the intelligent eyewear PPE device includes intelligent safety glasses, or the intelligent clothing PPE device includes an intelligent safety belt. In some embodiments, the safety incident includes a critical safety incident, and the response to the safety incident includes suspending operations of the industrial plant and alerting entities of the industrial plant system. In certain embodiments, the safety incident includes a moderate safety incident, and the response to the safety incident includes alerting entities of the industrial plant system. In some embodiments, the method includes an intelligent PPE system worn by a person located in the industrial plant receiving, from a smart device coupled to a plant device, environmental data indicative of a characteristic of the plant device, and the intelligent PPE system communicating the environmental data indicative of the characteristic of the plant device to the person by way of an EEG sensor of the intelligent PPE system.

Provided in some embodiments is a non-transitory computer readable medium including program instructions stored thereon that are executable by a processor to cause the following operation for operating an industrial plant: sensing, by one or more one or more intelligent personal protective equipment (PPE) systems worn by personnel located in an industrial plant, personal and environmental characteristics of the personnel, where each of the one or more intelligent PPE systems are worn by a person located in the industrial plant, where each of the intelligent PPE systems includes one or more intelligent PPE devices sensing personal and environmental characteristics of the person wearing the intelligent PPE system, and where the personal and environmental characteristics of the personnel include the personal and environmental characteristics sensed by the one or more intelligent PPE devices of the one or more intelligent PPE systems; transmitting, by the one or more PPE systems, safety data corresponding to the personal and environmental characteristics of the personnel; monitoring, by an industrial safety system (ISS), a safety status of the industrial plant, including: collecting, from the one or more intelligent PPE systems, the safety data; determining, based on the safety data collected, whether a safety incident has occurred; and in response to determining that a safety incident has occurred, executing a response to the safety incident.

Figure 1:
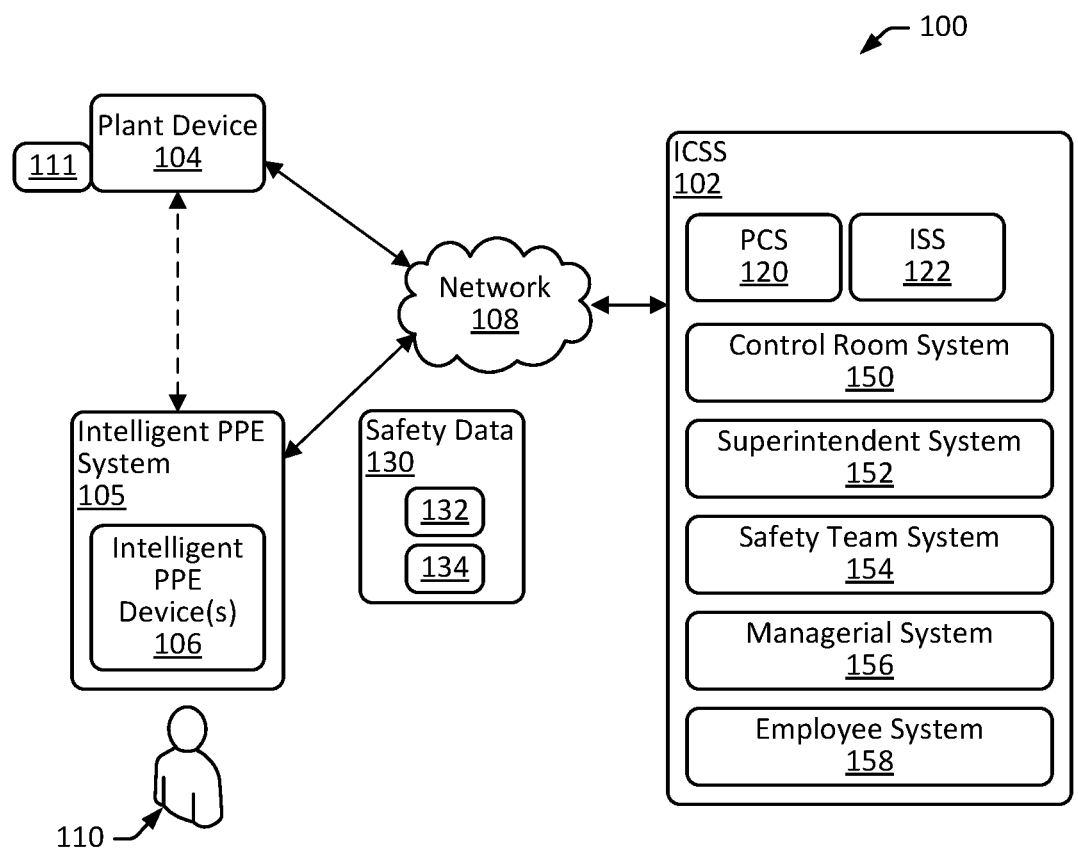
FIG. 1 is a diagram that illustrates an industrial plant environment in accordance with one or more embodiments.

While this disclosure is susceptible to various modifications and alternative forms, specific embodiments are shown by way of example in the drawings and will be described in detail. The drawings may not be to scale. It should be understood that the drawings and the detailed descriptions are not intended to limit the disclosure to the particular form disclosed, but are intended to disclose modifications, equivalents, and alternatives falling within the spirit and scope of the present disclosure as defined by the claims.

DETAILED DESCRIPTION

Described are embodiments of systems and methods for integrated control and safety systems (ICSSs) that employ intelligent personal protective equipment (PPE). In some embodiments, sensing devices of an industrial safety system (ISS) are integrated with PPE that is worn by employees during the course of their work duties. PPE can include safety equipment, such as safety helmets, gloves, safety glasses, shoes, belts and the like that are worn by employees during the course working at an industrial plant. In many instances, persons are mandated to wear these and other types of PPE while in the industrial plant environment. In some embodiments, the sensing devices integrated in an intelligent PPE system worn by a person are employed to collect safety data for the person, including personal health data and/or environmental data.

The personal health data may include biometric health data for the person, such as heart rate, body temperature, brain activity, stress level, physical exertion, blink rate, heart rate, sweat rate, body position and/or the like. The environmental data may include data regarding the environment surrounding the person, such as a geographic location of the person, a temperature at the location of the person, and information for devices proximate to the location of the person. The information for devices proximate to the location of the person can include, for example, information regarding the status, configuration, and operation of devices within communication range of the intelligent PPE. In some embodiments, the personal health data is collected via safety sensors integrated into the PPE or otherwise worn by the person, such as heart rate sensors, body temperature sensors, electroencephalography (EEG) sensors, galvanic skin response (GSR) sensors, pressure sensors, image sensors, and position sensors. In some embodiments, the environmental data is collected via environmental safety sensors integrated into the PPE or otherwise worn by the person, such as temperature sensors, location sensors and communication devices. The communication devices may enable the PPE to communicate with other devices proximate to the location and/or to communicate with an ISS via a network of the ICSS.

In some embodiments, an intelligent PPE device includes intelligent headwear. For example, an intelligent PPE device can include a safety helmet (or "hard-hat") that includes temperature sensors, EEG sensors, position sensors, location sensors, and/or a wireless communication device integrated therein. In some embodiments, an intelligent PPE device includes intelligent hand wear. For example, an intelligent PPE device can include safety gloves that include temperature sensors, pressure sensors, GSR sensors, heart rates sensors, position sensors, a location sensor, and a wireless communication device integrated therein. In some embodiments, an intelligent PPE device includes intelligent footwear. For example, an intelligent PPE device can include safety boots that include temperature sensors, pressure sensors, position sensors, location sensors, and wireless communication devices integrated therein. In some embodiments, intelligent PPE includes intelligent eyewear. For example, an intelligent PPE device can include safety glasses that include image sensors, temperature sensors, position sensors, a location sensor, and a wireless communication device integrated therein. In some embodiments, an intelligent PPE device includes an intelligent article of clothing. For example, an intelligent PPE device can include a safety belt that includes temperature sensors, position sensors, a location sensor, and a wireless communication device integrated therein. Although certain examples are provided for the purpose of explanation, embodiments can include various combinations of PPE devices and integrated sensors.

In some embodiments, safety data for one or more persons in an industrial plant is collected from intelligent PPEs worn by the one or more persons, and various plant safety operations are undertaken based on the safety data collected. For example, if a critical safety incident (or "safety event") for a particular portion of the industrial plant is determined from the safety data collected, the ICSS may take steps to shut down operations in that portion of the plant and provide corresponding alerts. In some embodiments, the ICSS for an industrial plant can include several different layers of control and monitoring, and different levels of response can be instituted based on the level of a safety incident. For example, the ICSS can provide feedback to systems for a control room, a superintendent, a safety team, managers and employees that all interact to provide for operation of an ICSS. In the event of a relatively low-level safety incident for a person, the ICSS may provide direct feedback to the person. For example, if the ICSS detects five instances of an employee engaging in poor posture, the ICSS may send a message to the employee. In the event of a relatively high-level safety incident, the ICSS may provide feedback to various portions of the ICSS, and may effectuate an action to remedy the incident. For example, if the ICSS detects a health crisis for a person, such as an elevated heart rate for an extended duration, the ICSS may notify the control room, the superintendent, the safety team, and the person's manager, and may initiate suspension of operations that rely on that person and that could further jeopardize the health of that person, such suspend the operation of machinery under control of the person and/or located near the person.

The integration of intelligent PPE and the use of safety data collected by way of the intelligent PPE can enhance the ability of an ICSS to collect relevant safety data across an industrial plant and, in turn, provide improvements in the ability to predict and resolve potential and actual safety incidents. As a result, the integration of intelligent PPE within the ICSS can certainly improve the effectiveness of the ICSS, and improve the safety of the working environment of industrial plants.

FIG. 1 is a diagram that illustrates an industrial plant environment ("industrial plant") 100 in accordance with one or more embodiments. In the illustrated embodiment, the industrial plant 100 includes an integrated control and safety system ("ICSS") 102, one or more industrial plant devices 104 and one or more personal intelligent PPE systems ("intelligent PPE systems") 105 (e.g., including one or more PPE devices 106) communicatively coupled by way of an industrial plant communications network ("network") 108. Each of the intelligent PPE systems 105 may include one or more intelligent PPE devices 106 worn by a person 110 present in the industrial plant 100, such as an employee working in the industrial plant 100. The industrial plant 100 can include any number of employees wearing an intelligent PPE system 105.

The network 108 may include an element or system that facilitates communication between the entities of the industrial plant 100. For example, the network 108 may include an electronic communications network, such as a local area network (LAN), a wide area network (WAN), a wireless local area network (WLAN), a cellular communications network, the Internet, an industrial network, and/or the like. In some embodiments, the network 108 can include a single network or a combination of networks.

The ICSS 102 can include a process control system (PCS) 120 and/or an industrial safety system (ISS) 122. The PCS 120 may control processes of the industrial plant 100. For example, the PCS 120 may monitor and control the operations of the industrial plant devices 104 to provide for the day-to-day operations of the industrial plant 100 under normal operating conditions. In the context the processing of produced oil and gas, for example, the PCS 120 may control various industrial plant devices 104, such as valves, pumps, and pressure vessels to separate a produced oil mixture into oil, gas and water. The ICSS 102 may include one or more computer systems similar to that of the computer system 1000 described with regard to at least FIG. 6.

The ISS 122 may control safety systems of the industrial plant 100. The ISS 122 may include safety sensors and controllers that monitor the safety status of the industrial plant 100 and, if needed, initiate action to ensure that any potential and actual safety issues at the industrial plant 100 are addressed. If, for example, the ISS 122 detects an exceedingly high pressure within a pressure vessel, the ISS 122 may command the PCS 120 to close an emergency shutdown (ESD) valve (to terminate a fluid supply to the pressure vessel) and command the PCS 120 to open a pressure safety valve (PSV) to prevent rupturing of the pressure vessel. The ISS 122 can take various forms, such as a process safety (or shutdown) systems (PSS) and/or a safety shutdown system (SSS), such as emergency shutdown (ESD) and/or emergency depressurization (EDP) system. In some embodiments, the ISS 122 monitors safety data 130 communicated from intelligent PPE devices 106, processes the safety data 130 to assess the safety status of the industrial plant 100 to identify any potential or actual safety issues (or "incidents"), and, if potential or actual safety issues are identified, takes action to alleviate the potential and/or actual safety incidents and/or alerts one or more entities of the ICSS 102 to the potential and/or actual safety incidents. The ISS 102 may include one or more computer systems similar to that of the computer system 1000 described with regard to at least FIG. 6.

The industrial plant devices 104 can include components for performing and/or monitoring operations of the industrial plant 100. For example, the plant devices 104 can include turbomachinery devices (e.g., turbines, generators, compressors and/or the like of machine systems), electrical system devices (e.g., electrical power generators, batteries, electrical cables and/or the like), flow control system devices (e.g., flow control valves, pressure vessels, pipes and/or the like) and/or sensing system devices (e.g., temperature sensors, pressures sensors, flow rate sensors and/or the like).

The intelligent PPE devices 106 can include PPE devices having safety sensors integrated therein, such as temperature sensors, EEG sensors, pressure sensors, GSR sensors, position sensors, image sensors, heart rate sensors, location sensors, wireless communication devices, and/or the like. An intelligent safety device 106 can be employed to collect safety data 130 for a person wearing the PPE device 106, including personal health data ("PHD") 132 and/or environmental data ("ED") 134 for the person 110. Personal health data 132 for a person 110 may include a body temperature for the person 110, brain activity for the person 110, forces exerted by or on the person 110, facial characteristics of the person 110, body position of the person 110, heart rate of the person 110, a blink rate for the person 110, a sweat rate for the person 110, and/or the like. Environmental data 134 for a person 110 may include environmental characteristics for the person 110, such as a geographic location of the person 110, an environmental temperature at the location of the person 110, information for devices proximate to the location of the person 110, and/or the like. In some embodiments, the environmental data 134 includes signals indicative various plant operations and conditions, such as inefficiencies in pipeline flow rates, alerts of required maintenance, and corrosion. In some embodiments, some or all of the environmental data 134 is provided directly to a PPE device 106 from a smart device 111 in the industrial plant 100. A smart device 111 may include, for example, a smart sensor mounted on a valve plant device 104 and adapted to transmit environmental data 134 indicative of operational characteristics of the valve, such as a flow rate through the valve, required maintenance for the valve, and corrosion detected at the valve.

In some embodiments, an intelligent PPE device 106 includes intelligent headwear. For example, an intelligent PPE device 106 can include a safety helmet (or "hard-hat") that includes temperature sensors, EEG sensors, position sensors, location sensors, and/or a wireless communication device integrated therein. Such an intelligent safety helmet may be capable of sensing safety data 130 for a person 110 wearing the safety helmet, including, for example, personal health data 132 for the person 110 (such as a body temperature at the head of the person 110, brain activity for the person 110, and a body position of the person 110), as well as environmental data 134 for the person 110 (such as a location of the person 110, an environmental temperature near the head of the person 110, and information for industrial plant devices 104 proximate to the location of the person 110).

In some embodiments, the industrial plant 100 includes smart devices 111. A smart device 111 may include a self-contained unit that is capable of collecting, processing and/or transmitting data. For example, a smart device 111 may include a sensor, a processor, a memory, and a wireless transmission device. Such a smart device 111 may, for example, use the sensor to collect environmental data, use the processor to analyze and store the data (in the memory), and transmit relevant information to other devices, such as the raw or processed data, or alerts relating to the data. In some embodiments, smart devices 111 mounted on plant devices 104, such as smart sensors mounted on valves, wirelessly communicate relevant plant information, such as signals indicative various plant operations and conditions (e.g., inefficiencies in pipeline flow rates, alerts of required maintenance, and corrosion), directly to a person 110 in the industrial plant 100 within wireless communication range of the smart device 111. This may be accomplished, for example, by way of wireless communication between the smart device 111 and EEG sensors provided in an intelligent headwear PPE device worn by the person 110. Thus, the person 110 may process relevant plant information received from a smart device 111 by way of the EEG sensors, and take actions to address any issues that are indicated by the information. For example, where a low flow rate, maintenance, or corrosion is indicated for a valve plant device 104, the person 110 may identify such an issued based on the information received from a smart device 111 on the valve by way of the EEG sensors in their intelligent headwear PPE device, and move to the valve plant device 104 to inspect the valve or take an action to remedy the issue (e.g., adjust the valve to increase a flow rate, conduct the required maintenance on the valve, or inspect for corrosion at the valve). The person 110 may report any issues indicated by the information, and any actions taken to remedy the issues, to the ICSS 102 or an entity thereof, such as a superintendent system. Similarly, such a configuration may also enable smart devices 111 to wirelessly communicate relevant plant information to the ICSS 102, for example, by way of an intelligent PPE system 105 within wireless communication range of the smart device 111 and the network 108.

Figure 2A:
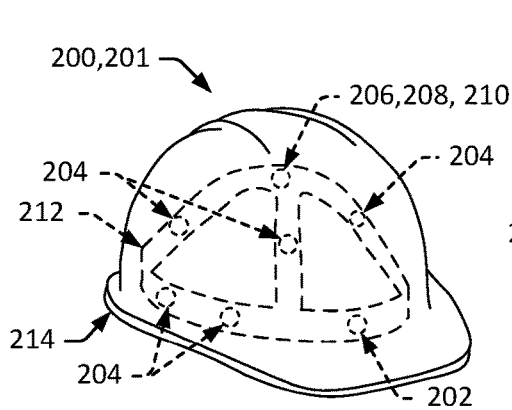
FIG. 2A is a diagram that illustrates intelligent headwear personal protective equipment (PPE) in accordance with one or more embodiments.

FIG. 2A is a diagram that illustrates an intelligent headwear PPE device 200 in accordance with one or more embodiments. In the illustrated embodiment, the intelligent headwear PPE device 200 includes a safety helmet 201 having a temperature sensor 202, EEG sensors 204, a position sensor 206, a location sensor 208, and a wireless communication device 210 integrated therein. The safety helmet 201 may include a shell 214 and a headband 212 disposed inside of the shell 214. The headband 212 may be arranged to secure the safety helmet 201 to the head of a person wearing the safety helmet 201.

The temperature sensor 202 may be arranged to sense and report a body temperature of a head of a person wearing the safety helmet 201. In some embodiments, the temperature sensor 202 is arranged to contact a head of a person wearing the safety helmet 201. For example, the temperature sensor 202 may be disposed on an interior surface of the headband 212 of the safety helmet 201, such that temperature sensor 202 contacts the head of a person wearing the safety helmet 201.

The EEG sensors 204 may be arranged to sense and report brain activity of a person wearing the safety helmet 201. In some embodiments, the EEG sensors 204 are arranged to contact a scalp of a person wearing the safety helmet 201. For example, the EEG sensors 204 may be disposed on an interior surface of the headband 212 of the safety helmet 201 such that the EEG sensors 204 contact a scalp of a person wearing the safety helmet 201.

The position sensor 206 may sense and report a position of the safety helmet 201 in three dimensional space. Such position information may be used, for example, to determine a position and/or movement of a head of a person wearing the safety helmet 201 relative to other portions of the body of the person, such as the hands, waist, and feet of the person. In some embodiments, the position sensor 206 is disposed on the headband 212 or shell 214 of the safety helmet 201. For example, the position sensor 206 may be disposed on a top/central portion of the headband 212 or shell 214 such that it is located just above the top/central portion of the head of a person wearing the safety helmet 201. Such positioning of the position sensor 206 may provide for sensing and reporting a position of a top/central portion of the head of the person. Such head position information can be useful, for example, for determining an alignment of the head of the person relative to other portions of the person's body.

The location sensor 208 may include a sensor (e.g., a global positioning system (GPS) sensor) for determining a geographic location of the safety helmet 201. Such geographic location information may be used, for example, to determine a geographic location of a person wearing the safety helmet 201. In some embodiments, the location sensor 208 is disposed on the headband 212 or shell 214 of the safety helmet 201. For example, the location sensor 208 may be disposed on an exterior, top/central portion of the shell 214. Such positioning of the location sensor 208 may provide for improved reception of GPS satellite signals. As another example, the location sensor 208 may be disposed on an interior, top/central portion of the shell 214. Such positioning of the location sensor 208 may provide for improved reception of GPS satellite signals, as well as for protection of the location sensor 208 from environmental conditions, such as impacts, rain, and/or the like.

The wireless communication device 210 may include a wireless communication module that is capable of communicating with the network 108, plant devices 104 and/or other PPE devices 106. For example, the wireless communication device 210 may include a relatively long-range communication module that is capable of communicating with the network 108 and/or a relatively short-range communication module that is capable of communicating with plant devices 104 and/or other PPE devices 106. For example, with regard to relatively long-range communication, the wireless communication device 210 may include a Wi-Fi enabled communication module that is capable of communicating with the network 108 via Wi-Fi communication protocols. With regard to relatively short-range communication, the wireless communication device 210 may include a Bluetooth enabled communication module that is capable of communicating with plant devices 104 and/or other PPE devices 106 via Bluetooth wireless communication protocols. Communication with the network 108 may enable the safety data 130 collected via the sensors of the safety helmet 201 to be communicated to the other entities of the industrial plant 100, such as the ICSS 102. Communication with the plant devices 104 may enable the safety helmet 201 to receive device information directly from nearby plant devices 104 and/or act as an intermediary to communicate data between nearby plant devices 104 and other entities of the industrial plant 100, such as the ICSS 102. In some embodiments, the wireless communication device 210 is disposed on the headband 212 or shell 214 of the safety helmet 201. For example, the wireless communication device 210 may be disposed on an exterior, top/central portion of the shell 214. Such positioning of the wireless communication device 210 may provide for improved reception of wireless signals. As a another example, the wireless communication device 210 may be disposed on an interior, top/central portion of the shell 214. Such positioning of the wireless communication device 210 may provide for improved reception of wireless signals, as well as for the protection of the wireless communication device 210 from environmental conditions, such as impacts, rain, high and low temperatures and/or the like.

In some embodiments, an intelligent PPE device 106 includes intelligent hand wear. For example, an intelligent PPE device 106 can include safety gloves that include temperature sensors, pressure sensors, GSR sensors, heart rates sensors, position sensors, a location sensor, and a wireless communication device integrated therein. Such intelligent safety gloves may be capable of sensing safety data 130 for a person 110 wearing the safety gloves, including, for example, personal health data 132 for the person 110 (such as a body temperature at the hands of the person 110, forces exerted on or by the hands of the person 110, electrical conductance of the skin of the hands of the person 110, a heart rate of the person 110, and hand positions of the person 110), as well as environmental data 134 for the person 110 (such as a geographic location of the person 110, an environmental temperature near the hands of the person 110, and information for devices proximate to the location of the person 110).

Figure 2B:
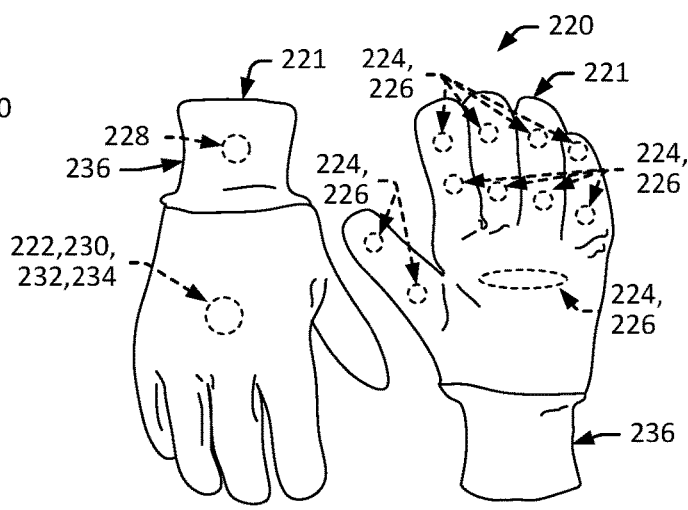
FIG. 2B is a diagram that illustrates intelligent hand wear PPE in accordance with one or more embodiments.

FIG. 2B is a diagram that illustrates an intelligent hand wear PPE device 220 in accordance with one or more embodiments. In the illustrated embodiment, the intelligent hand wear PPE device 220 includes a pair of safety gloves 221 (including right and left safety gloves 221) each having temperature sensors 222, pressure sensors 224, GSR sensors 226, a heart rate sensor 228, a position sensors 230, a location sensor 232, and a wireless communication device 234 integrated therein. The safety gloves 221 may include a suitable material, such as cloth or leather, for covering the fingers, palm and wrist of a person wearing the safety gloves 221.

The temperature sensors 222 may be arranged to sense and report a body temperature of hands of a person wearing the safety gloves 221. In some embodiments, the temperature sensors 222 are arranged to contact the hands of a person wearing the safety gloves 221. A temperature sensor 222 may be located in one or both of the left and right gloves 221 of the pair of safety gloves 221. In some embodiments, the temperature sensor 222 of a safety glove is disposed on an interior surface of a top side of the safety glove 221 (opposite a palm side of the safety glove 221). Such an arrangement of the temperature sensor 222 may enable the temperature sensor 222 to accurately sense a temperature of a top side of a hand of a person wearing the safety glove 221, without the sensed temperature being skewed by temperature of an item held in or otherwise contacting a palm of the safety glove 221.

The pressure sensors 224 may be arranged to sense and report forces exerted on or by hands of a person wearing the safety gloves 221. In some embodiments, the pressure sensors 224 are arranged to reside between the hands of a person wearing the safety gloves 221 and items contacted by the safety glove 221 (e.g., gripped by the hands of the person wearing the safety gloves 221), such that the pressure sensors 224 can measure a force exerted on or by hands of a person wearing the safety gloves 221. In some embodiments, the pressure sensors 224 of a safety glove 221 are disposed on an interior surface of the safety glove 221 or integrated into the material of the safety glove 221. Such an arrangement may enable the pressure sensors 224 to measure forces exerted on or by hands of a person wearing the safety gloves 221, as well as protect the pressure sensors 224 from environmental conditions, such as rain, high and low temperatures, and/or the like. In some embodiments, the pressure sensors 224 of a safety glove 221 are located at discrete locations about the safety glove 221 to sense forces exerted on or by hands corresponding portions of the hand on which the safety gloves 221 is disposed. For example, the pressure sensors 224 may be located on a palm side of some or all of the five fingers of the safety glove 221 and/or in the palm of the safety glove 221. Such an arrangement of pressure sensors 224 may enable measurement of a gripping force exerted by each of the respective fingers and/or a gripping force exerted by the palm of a person wearing the safety glove 221.

The GSR sensors 226 may be arranged to sense and report skin conductance (or "galvanic skin response") of hands of a person wearing the safety gloves 221. The electrical conductance of the skin, which varies with its moisture level, may be used, for example, to determine a level of sweating of the person wearing the safety gloves 221. The determined level of sweating can, in turn, be used to identify a stress level of the person wearing the safety gloves 221. For example, a measured increase in the electrical conductance of the skin (measured by the GSR sensors 226 of the safety gloves 221) to a level above a threshold may be used to identify that a person wearing the safety gloves 221 is experiencing relatively high stress. In some embodiments, the GSR sensors 226 of a safety glove 221 are located at discrete locations about the safety glove 221 to sense electrical conductance of the skin of corresponding portions of the hand on which the safety gloves 221 is disposed. For example, the GSR sensors 226 may be located on a palm side of some or all of the five fingers of the safety glove 221 and/or in the palm of the safety glove 221. Such an arrangement of GSR sensors 226 may enable measurement of the electrical conductance of the fingers and the palm of a person wearing the safety glove 221. In some embodiments, the GSR sensors 226 may be located in a portion of the safety glove 221 that can provide a measurement of electrical conductance of the skin, while being protected from environmental conditions, such as impacts or relatively high forces. For example, the safety glove 221 may include only GSR sensors 226 located in the pinkie finger of the safety glove 221, with the expectation that the pinkie finger will experience a relatively low level of impacts and gripping forces when compared to other fingers.

The heart rate sensor 228 may be arranged to sense and report a heart rate of a person wearing the safety gloves 221. In some embodiments, the heart rate sensor 228 of a safety glove 221 may be located in a portion of the glove adjacent the wrist of the person wearing the safety glove 221. For example, the heart rate sensor 228 may include an optical heart rate sensor located in a wrist portion of the safety glove 221. The optical heart rate sensor may include light emitting diodes (LEDs) that are arranged to shine light into the wrist of the person wearing the safety glove 221, and an optical sensor to measure the amount of light that is scattered by blood flow in the wrist of the person. Light may be scattered in a given manner by dynamic changes in blood flow, such as the pulse of flow caused by a beat of the heart and, thus, the measured changes in the light scattering can be used to determine the heart rate of the person wearing the safety glove 221. In some embodiments, the heart rate sensor 228 is arranged to be held near or against the skin of the person wearing the safety glove 221 to enhance the measurement of heart rate. For example, the heart rate sensor 228 may include LEDs and optical sensors located at or near an elastic band 236 of the wrist portion of the safety glove 221 that holds the LEDs and optical sensors near or against the skin of the wrist of a person wearing the safety glove 221.

The position sensors 230 may sense and report a position of the safety gloves 221 in three dimensional space. Such position information may be used, for example, to determine a position and/or movement of the hands of a person wearing the safety gloves 221 relative to other portions of the body of the person, such as the head, waist, and feet of the person. In some embodiments, the position sensor 230 for a safety glove 221 is disposed on a top side of the safety glove 221 (opposite a palm side of the safety glove 221). Such a positioning of the position sensor 230 may help to protect the location sensor 208 from environmental conditions, such as impacts, and gripping forces at the palm side of the safety glove 221. In some embodiments, the position sensor 230 for a safety glove 221 includes a flex sensor arranged to acquire measurements of wrist angle. The wrist angle may be indicative of an angle of the hand relative to the angle of the forearm of the person. In such an embodiment, the position sensor 230 for the safety glove 221 may be disposed proximate the wrist of the person. For example, the position sensor 230 may be on a top side of the elastic band 236 of the safety glove 221.

The location sensor 232 may include a sensor (e.g., a GPS sensor) for determining a geographic location of the safety gloves 221. Such geographic location information may be used, for example, to determine a geographic location of a person wearing the safety gloves 221. In some embodiments, the location sensor 232 for a safety glove 221 is disposed on a top side of the safety glove 221 (opposite a palm side of the safety glove 221). Such positioning of the location sensor 232 may provide for improved reception of GPS satellite signals, as well as for protection of the location sensor 232 from environmental conditions, such as impacts, and gripping forces at the palm side of the safety glove 221.

The wireless communication device 234 may include a wireless communication module that is capable of communicating with the network 108, plant devices 104 and/or other PPE devices 106. For example, the wireless communication device 234 may include a relatively long-range communication module that is capable of communicating with the network 108 and/or a relatively short-range communication module that is capable of communicating with plant devices 104 and/or other PPE devices 106. For example, with regard to relatively long-range communication, the wireless communication device 234 may include a Wi-Fi enabled communication module that is capable of communicating with the network 108 via Wi-Fi communication protocols. With regard to relatively short-range communication, the wireless communication device 234 may include a Bluetooth enabled communication module that is capable of communicating with plant devices 104 and/or other PPE devices 106, via Bluetooth wireless communication protocols. Communication with the network 108 may enable safety data 130 collected via the sensors of the safety gloves 221 to be communicated to the other entities of the industrial plant 100, such as the ICSS 102. Communication with the plant devices 104 may enable the safety gloves 221 to receive device information directly from nearby plant devices 104 and/or act as an intermediary to communicate data between nearby plant devices 104 and other entities of the industrial plant 100, such as the ICSS 102. A wireless communication device 234 may be located in one or both of the left and right gloves of the pair of safety gloves 221. In some embodiments, the wireless communication device 234 for a safety glove 221 is disposed on a top side of the safety glove 221 (opposite a palm side of the safety glove 221). Such positioning of the wireless communication device 234 may provide for improved reception of wireless signals, as well as for protection of the wireless communication device 234 from environmental conditions, such as impacts and gripping forces at the palm side of the safety glove 221.

In some embodiments, an intelligent PPE device 106 includes intelligent footwear. For example, an intelligent PPE device 106 can include safety boots (or shoes) that include temperature sensors, pressure sensors, position sensors, location sensors, and wireless communication devices integrated therein. Such intelligent safety boots may be capable of sensing safety data 130 for a person 110, including, for example, personal health data 132 for the person 110 (such as a body temperature at the feet of the person 110, forces exerted on or by the feet of the person 110, and foot position of the person 110), as well as environmental data 134 for the person 110 (such as a location of the person 110, an environmental temperature near the feet of the person 110, and information for devices proximate to the location of the person 110).

Figure 2C:
FIG. 2C is a diagram that illustrates intelligent footwear PPE in accordance with one or more embodiments.

FIG. 2C is a diagram that illustrates an intelligent footwear PPE device 240 in accordance with one or more embodiments. In the illustrated embodiment, the intelligent footwear PPE device 240 includes a pair of safety boots 241 (a right boot 241 of the pair of boots 241 being depicted) having temperature sensors 242, pressure sensors 244, position sensors 246, location sensors 248, and wireless communication devices 250 integrated therein.

The temperature sensor 242 may be arranged to sense and report a body temperature of hands of a person wearing the safety boots 241. In some embodiments, the temperature sensors 242 are arranged to contact feet of a person wearing the safety boots 241. Temperature sensors 242 may be located in one or both of the left and right boots of the pair of safety boots 241. In some embodiments, the temperature sensor 242 of a safety boot is disposed on a surface of the safety boot 241 arranged to contact and support an underside of a foot positioned in the safety boot 241, such as in insole of the safety boot 241. Such an arrangement of the temperature sensor 242 may enable the temperature sensors 242 to accurately sense a temperature of a bottom side of a foot of a person wearing the safety boots 242, without the sensed temperature being skewed by temperature of the environment around the safety boot 242.

The pressure sensor 244 may be arranged to sense and report forces exerted on or by feet of a person wearing the safety boots 241. In some embodiments, the pressure sensor 244 is arranged to reside between sole of the foot of a person wearing the safety boot 241 and a support surface, such that the pressure sensor 244 can measure a force exerted on or by the foot of a person wearing the safety boot 241, for example, while walking or standing. In some embodiments, the pressure sensor 244 is disposed on a surface of the safety boot 241 arranged to contact and support an underside of a foot positioned in the safety boot 241, such as on a heel portion and/or a forefoot portion of an insole of the safety boot 241. With the pressure sensor 244 positioned in the heel portion and the forefoot portion of an insole of the safety boot 241, forces sensed at the pressure sensor 244 at the heel portion and forces sensed at the pressure sensor 244 at the forefoot portion can be added to determine a total force supported by the foot and the safety boot 241, and the forces for each safety boot 241 of a par of safety boots 241 can be added to determine a total force supported by the safety boots 241. The total force may be indicative of a weight of the person wearing the pair of safety boots 241, or a reactionary force caused by the person lifting an object, turning a valve, and/or the like.

The position sensor 246 may sense and report a position of the safety boot 241 in three dimensional space. Such position information may be used, for example, to determine a position and/or movement of the foot of a person wearing the safety boot 241 relative to other portions of the body of the person, such as the head, waist, and hands of the person. In some embodiments, the position sensor 246 is disposed proximate the heel or ankle of the safety boot 241, such as in the heel portion of an insole of the safety boot 241. Such a positioning of the position sensors 246 may provide for sensing and reporting a position of the ankle or heel of the person. Such ankle or heel position information can be useful, for example, for determining an alignment of the feet and legs of the person relative to other portions of the person's body.

The location sensor 248 may include a sensor (e.g., a GPS sensor) for determining a geographic location of the safety boots 241. Such geographic location information may be used, for example, to determine a geographic location of a person wearing the safety boots 241. In some embodiments, the location sensor 248 for a safety boot 241 is disposed on a top portion of the safety boot 241 (e.g., on a cuff portion of the safety boot 241). Such positioning of the location sensor 248 may provide for improved reception of GPS satellite signals, as well as for protection of the location sensor 248 from environmental conditions, such as impacts, and other forces acting on the foot portion of the safety boot 241.

The wireless communication device 250 may include a wireless communication module that is capable of communicating with the network 108, plant devices 104 and/or other PPE devices 106. For example, the wireless communication device 250 may include a relatively long-range communication module that is capable of communicating with the network 108 and/or a relatively short-range communication module that is capable of communicating with plant devices 104 and/or other PPE devices 106. For example, with regard to relatively long-range communication, the wireless communication device 250 may include a Wi-Fi enabled communication module that is capable of communicating with the network 108 via Wi-Fi communication protocols. With regard to relatively short-range communication, the wireless communication device 250 may include a Bluetooth enabled communication module that is capable of communicating with plant devices 104 and/or other PPE devices 106 worn by a person, via Bluetooth wireless communication protocols. Communication with the network 108 may enable the communication of safety information collected via the sensors of the safety boots 241 to be communicated to the other entities of the industrial plant 100, such as the ICSS 102. Communication with the plant devices 104 may enable the safety boots 241 to receive device information directly from nearby plant devices 104 and/or act as an intermediary to communicate data between nearby plant devices 104 and other entities of the industrial plant 100, such as the ICSS 102. A wireless communication device 250 may be located in one or both of the left and right boots 241 of the pair of safety boots 241. In some embodiments, the wireless communication device 250 for a safety boot 241 is disposed on a top portion of the safety boot 241 (e.g., on a cuff portion of the safety boot 241). Such positioning of the wireless communication device 250 may provide for improved reception of GPS satellite signals, as well as for protection of the wireless communication device 250 from environmental conditions, such as impacts and other forces acting on the foot portion of the safety boot 241.

In some embodiments, an intelligent PPE device 106 includes intelligent eyewear. For example, an intelligent PPE device 106 can include safety glasses that include image sensors, temperature sensors, position sensors, a location sensor, and a wireless communication device integrated therein. Such intelligent safety glasses may be capable of sensing safety data 130 for a person 110, including, for example, personal health data 132 for the person 110 (such as a body temperature at the head of the person 110, facial characteristics (such a blink rate) of the person 110, and a head position of the person 110), as well as environmental data 134 for the person 110 (such as a location of the person 110, an environmental temperature near the face of the person 110, and information for devices proximate to the location of the person 110).

Figure 2D:
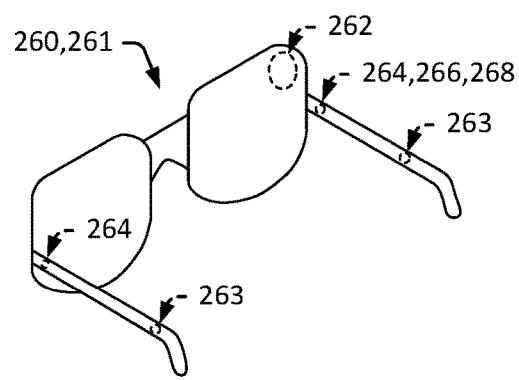
FIG. 2D is a diagram that illustrates intelligent eyewear PPE in accordance with one or more embodiments.

FIG. 2D is a diagram that illustrates an intelligent eyewear PPE device 260 in accordance with one or more embodiments. In the illustrated embodiment, the intelligent eyewear PPE device 260 includes safety glasses 261 having an image sensor 262, temperature sensors 263, position sensors 264, a location sensor 266, and wireless communication device 268 integrated therein.

The image sensor 262 may be arranged to acquire images of the face and eyes of a person wearing the safety glasses 261. The images may be used to determine various characteristics of the person, such as a blink rate of the eyes of the person, facial expressions of the person, and/or the like. In some embodiments, the image sensor 262 may include a camera integrated into the frame or lens of the safety glasses 261 and having a field of view directed to the face of the person such that the images capture a depiction of one or both of the person's eyes.

The temperature sensor 263 may be arranged to sense and report a body temperature of the head of a person wearing the safety glasses 261. In some embodiments, the temperature sensors 263 are arranged to contact the side of the head of the person wearing the safety glasses 261. Temperature sensors 263 may be located on one or both of the left and right arms of the safety glasses 261. In some embodiments, the temperature sensor 263 of safety glasses 261 are arranged to contact the side of the head of the person, for example, near the temple or ear of the person.

The position sensors 264 may sense and report a position of the safety glasses 261 in three dimensional space. Such position information may be used, for example, to determine a position and/or movement of the head of a person wearing the safety glasses 261 relative to other portions of the body of the person, such as the hands, waist, and feet of the person. In some embodiments, the position sensor 264 of the safety glasses 261 is disposed on one or both of the left and right arms of the safety glasses 261. For example, the position sensors 264 may be disposed near the point where the arms meet the frame portion of the safety glasses 261. Such positioning of the position sensors 264 may provide for sensing and reporting a position and orientation the head of the person. Such head position information can be useful, for example, for determining an alignment of the head of the person relative to other portions of the person's body.

The location sensor 266 may include a sensor (e.g., a GPS sensor) for determining a geographic location of the safety glasses 261. Such geographic location information may be used, for example, to determine a geographic location of a person wearing the safety glasses 261. In some embodiments, the location sensor 266 is disposed on the arms of the safety glasses 261. For example, the location sensor 266 may be disposed near the point where the arms meet the frame portion of the safety glasses 261. Such positioning of the location sensor 266 may provide for improved reception of GPS satellite signals.

The wireless communication device 268 may include a wireless communication module that is capable of communicating with the network 108, plant devices 104 and/or other PPE devices 106. For example, the wireless communication device 268 may include a relatively long-range communication module that is capable of communicating with the network 108 and/or a relatively short-range communication module that is capable of communicating with plant devices 104 and/or other PPE devices 106. For example, with regard to relatively long-range communication, the wireless communication device 268 may include a Wi-Fi enabled communication module that is capable of communicating with the network 108 via Wi-Fi communication protocols. With regard to relatively short-range communication, the wireless communication device 268 may include a Bluetooth enabled communication module that is capable of communicating with plant devices 104 and/or other PPE devices 106 worn by a person, via Bluetooth wireless communication protocols. Communication with the network 108 may enable the communication of safety information collected via the sensors of the safety glasses 261 to be communicated to the other entities of the industrial plant 100, such as the ICSS 102. Communication with the plant devices 104 may enable the safety glasses 261 to receive device information directly from nearby plant devices 104 and/or act as an intermediary to communicate data between nearby plant devices 104 and other entities of the industrial plant 100, such as the ICSS 102. In some embodiments, the wireless communication device 268 is disposed on the arms of the safety glasses 261. For example, the wireless communication device 268 may be disposed near the point where the arms meet the frame portion of the safety glasses 261. Such positioning of the wireless communication device 268 may provide for improved reception of wireless signals.

In some embodiments, an intelligent PPE device 106 includes an intelligent article of clothing. For example, an intelligent PPE device 106 can include a safety belt that includes temperature sensors, position sensors, a location sensor, and a wireless communication device integrated therein. Such an intelligent safety belt may be capable of sensing safety data 130 for a person 110, including, for example, personal health data 132 for the person 110 (such as a body temperature at the waist of the person 110, waist positioning of the person 110), as well as environmental data for the person 110 (such as a location of the person 110, an environmental temperature near the waist of the person 110, and information for devices proximate to the location of the person 110).

Figure 2E:
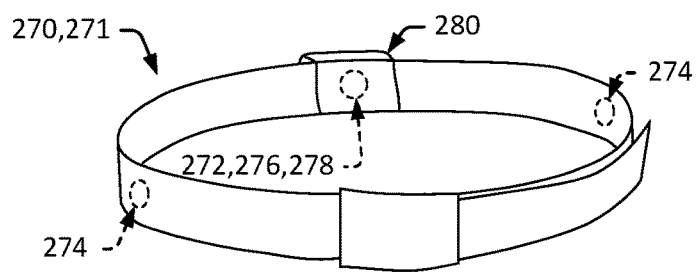
FIG. 2E is a diagram that illustrates intelligent clothing PPE in accordance with one or more embodiments.

FIG. 2E is a diagram that illustrates an intelligent clothing PPE device 270 in accordance with one or more embodiments. In the illustrated embodiment, the intelligent clothing PPE device 270 includes a safety belt 271 having a temperature sensor 272, position sensors 274, a location sensor 276, a wireless communication device 278, and a sensor module 280 integrated therein.

The sensor module 280 may include an enclosure that houses various sensors of the safety belt 271, such as the temperature sensor 272, the position sensors 274, the location sensor 276 and the wireless communication device 278. The sensor module 280 may be located such that it resides at or near the center of the back of the person. For example, the sensor module 274 may be located about half-way along the length of the safety belt 271. In some embodiments, the position of the sensor module 274 is adjustable. For example, the sensor module 274 may slide along the length of the belt so that its position can be adjusted.

The temperature sensor 272 may be arranged to sense and report a body temperature at a waist of the person wearing the safety belt 271. In some embodiments, the temperature sensor 272 is arranged to contact the waist of the person wearing the safety belt 271. Temperature sensor 272 may be located on an interior surface of the safety belt 271 arranged to abut the clothing or skin of the person at or near the waist of the person. In some embodiments, the temperature sensor 271 is disposed on an interior surface of a sensor module 280, arranged to abut the skin or the clothing of the person (e.g., contact an exterior surface of pants worn by the person) at or near the waist of the person.

The position sensors 274 may sense and report a position of the waist of the in three dimensional space. Such position information may be used, for example, to determine a position of the waist of a person wearing the safety belt 271 relative to other portions of the body of the person, such as the head, hands, and feet of the person. In some embodiments, position sensors 274 of the safety belt 271 are disposed at or near the left and right hips of the person. For example, right and left position sensors 274 may be positioned on the portion of the safety belt 271 at or near the right and left hips, respectively, of the person. Such positioning of the position sensors 274 may provide for sensing and reporting a position and orientation the hips of the person. Such hip position information can be useful, for example, for determining an alignment and/or movement of the hips of the person relative to other portions of the person's body. In some embodiments, each of the right and left position sensors 274 may include flex sensors arranged to acquire measurements of hip angle. The hip angle may be indicative of an angle of the upper leg relative to the angle of the torso of the person.

The location sensor 276 may include a sensor (e.g., a global positioning system (GPS) sensor) for determining a geographic location of the safety belt 271. Such geographic location information may be used, for example, to determine a geographic location of a person wearing the safety belt 271. In some embodiments, the location sensor 276 is disposed in a housing of the sensor module 280. Such positioning of the location sensor 266 may provide for improved reception of GPS satellite signals, as well as for protection of the location sensor 208 from environmental conditions, such as impacts, rain, high and low temperatures, and/or the like.

The wireless communication device 278 may include a wireless communication module that is capable of communicating with the network 108, plant devices 104 and/or other PPE devices 106. For example, the wireless communication device 278 may include a relatively long-range communication module that is capable of communicating with the network 108 and/or a relatively short-range communication module that is capable of communicating with plant devices 104 and/or other PPE devices 106. For example, with regard to relatively long-range communication, the wireless communication device 278 may include a Wi-Fi enabled communication module that is capable of communicating with the network 108 via Wi-Fi communication protocols. With regard to relatively short-range communication, the wireless communication device 278 may include a Bluetooth enabled communication module that is capable of communicating with plant devices 104 and/or other PPE devices 106 worn by a person, via Bluetooth wireless communication protocols. Communication with the network 108 may enable the communication of safety information collected via the sensors of the safety belt 271 to be communicated to the other entities of the industrial plant 100, such as the ICSS 102. Communication with the plant devices 104 may enable the safety belt 271 to receive device information directly from nearby plant devices 104 and/or act as an intermediary to communicate data between nearby plant devices 104 and other entities of the industrial plant 100, such as the ICSS 102. In some embodiments, the location sensor 276 is disposed in a housing of the sensor module 280. Such positioning of the location sensor 266 may provide for improved reception of wireless signals, as well as for protection of the location sensor 208 from environmental conditions, such as impacts, rain, high and low temperatures, and/or the like.

Figure 3:
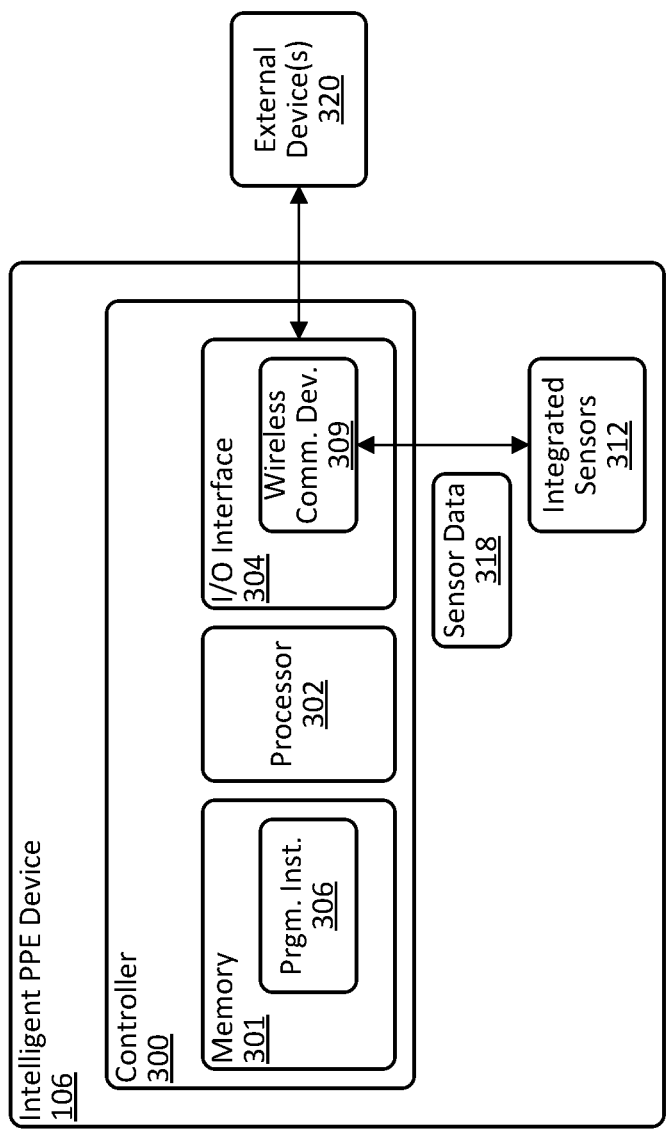
FIG. 3 is a block diagram that illustrates components of an intelligent PPE device in accordance with one or more embodiments.

FIG. 3 is a block diagram that illustrates components of an intelligent PPE device 106 in accordance with one or more embodiments of the present invention. Each of the intelligent headwear PPE device 200, the intelligent hand wear PPE device 220, the intelligent footwear PPE device 240, the intelligent eyewear PPE device 260, and/or the intelligent clothing PPE device 270 may have a configuration that is the same or similar to that of the intelligent PPE device of FIG. 3.

In some embodiments, the intelligent PPE device 106 includes an intelligent PPE device controller ("controller") 300 for controlling the operational aspects of the intelligent PPE device 106. For example, the controller 300 may provide for allocating power to integrated devices, collecting safety data 130 for a person 110 wearing the PPE device 106 and/or transmitting the collected safety data 130 to the ICSS 102. In some embodiments, the device controller 300 includes memory 301, a processor 302 and an input/output (I/O) interface 304.

The memory 301 may include non-volatile memory (e.g., flash memory, read-only memory (ROM), programmable read-only memory (PROM), erasable programmable read-only memory (EPROM), electrically erasable programmable read-only memory (EEPROM), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 301 may include a non-transitory computer readable storage medium having program instructions 306 stored thereon that are executable by a computer processor (e.g., the processor 304) to cause the functional operations (e.g., methods, routines and/or operational processes) for the intelligent PPE device 106.

The processor 302 may be any suitable processor capable of executing/performing program instructions. The processor 302 may include a central processing unit (CPU) that carries out program instructions (e.g., of the intelligent PPE device module 308) to perform arithmetical, logical, and input/output operations of the intelligent PPE device 106, including those described herein.

The I/O interface 304 may provide an interface for connection of one or more I/O devices to the controller 300. The I/O interface may include a wireless communication device 309. The wireless communication device 309 may include a relatively long-range communication module and/or a relatively short-range communication module. For example, with regard to relatively long-range communication, the wireless communication device 309 may include a Wi-Fi enabled communication module that is capable of communicating with external devices 320, such as the network 108 and the ICSS 102, via Wi-Fi communication protocols. With regard to relatively short-range communication, the wireless communication device 309 may include a Bluetooth enabled communication module that is capable of communicating with plant devices 104, other PPE devices 106 and/or integrated sensors 314, via Bluetooth wireless communication protocols. The wireless communication device 309 may include the wireless communication devices described with regard to the respective intelligent PPE devices 106 described herein. For example, where the intelligent PPE device 106 is an intelligent headwear PPE device 200, the wireless communication device 309 may include the wireless communication device 210.

I/O devices may include integrated I/O components (e.g., buttons, microphone, speaker, graphical display, and/or the like) 310, a power source (e.g., a battery) 312, integrated sensors 314, external devices 320 (e.g., plant devices 104, other intelligent PPE devices 106, the ICSS 102), and/or the like.

The integrated sensors 314 may include the integrated sensors of the respective intelligent PPE devices 106 described herein, such as temperature sensors, EEG sensors, pressure sensors, GSR sensors, position sensors, image sensors, location sensors, wireless communication devices, and/or the like physically integrated with the intelligent PPE device 106. For example, where the intelligent PPE device 106 is an intelligent headwear PPE device 200, the integrated sensors 314 may include the temperature sensor 202, the EEG sensors 204, the position sensor 206, the location sensor 208, and the I/O interface 304 may include the wireless communication device 210. The integrated sensors 314 and/or the external devices 320 may be connected to I/O interface 304 via a wired or wireless connection. For example, the external devices 320 may be connected to the I/O interface via wireless connection to the network 108.

The processor 302 of an intelligent PPE device 106 may be employed to collect the data from the various integrated sensors 314 and/or forward corresponding safety data 130 to the ICSS 102 for use in monitoring the safety conditions of the industrial plant 100. For example, each of the sensors 314 may forward sensor data 318 to the processor 302 via the I/O interface 304, the processor may assemble safety data 130 that includes the sensor data 318 (e.g., sensor measurements) received from the sensors 314, and the processor 302 may transmit the safety data 130 to the ICSS 102 via a WiFi connection with the network 108, using a Wi-Fi communication module of the wireless communication device 309.

Figure 4:
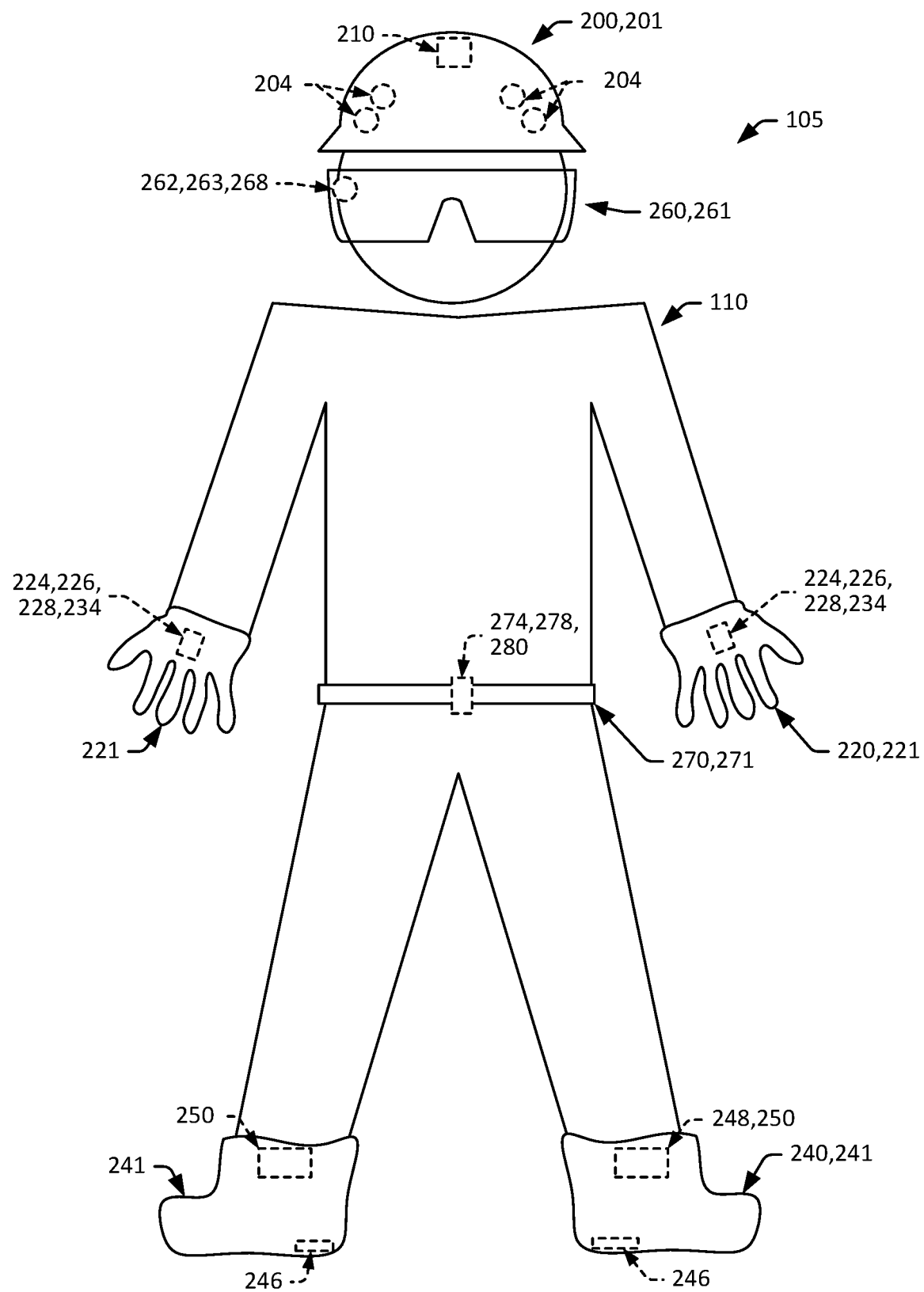
FIG. 4 is a diagram that illustrates a personal intelligent PPE system in accordance with one or more embodiments.

Embodiments can include various combinations of PPE devices 106 and integrated sensors. FIG. 4 is a diagram that illustrates an example embodiment of a personal intelligent PPE system 105 that worn by a person 110, including an example combination of PPE devices 106 and integrated sensors, in accordance with one or more embodiments. In the illustrated embodiment, the intelligent PPE system 105 includes an intelligent headwear PPE device 200, an intelligent hand wear PPE device 220, an intelligent footwear PPE device 240, an intelligent eyewear PPE device 260, and an intelligent clothing PPE device 270. The intelligent headwear PPE device 200 includes a safety helmet 201 having a EEG sensors 204 and a wireless communication device 210 integrated therein. The intelligent hand wear PPE device 220 includes a pair of safety gloves 221 having pressure sensors 224, GSR sensors 226, heart rate sensors 228, and wireless communication devices 234 integrated therein. The intelligent footwear PPE device 240 includes a pair of safety boots 241 having position sensors 246, a location sensor 248, and wireless communication devices 250 integrated therein. The intelligent eyewear PPE device 260 includes safety glasses 261 having an image sensor 262, temperature sensors 263 and a wireless communication device 268 integrated therein. The intelligent clothing PPE device 270 includes a safety belt 271 having a position sensors 274 and a wireless communication device 278 integrated in a sensor module 280. In some embodiments, each of the PPE devices 106 may communicate directly with the ICSS 102. For example, each of the intelligent headwear PPE device 200, the intelligent hand wear PPE device 220, the intelligent footwear PPE device 240, the intelligent eyewear PPE device 260, and the intelligent clothing PPE device 270 may communicate respective sets of safety data 130 to the ICSS 102 (e.g., via a WiFi connection to the network 108). In some embodiments, at least some of the PPE devices 106 may communicate indirectly with the ICSS 102. For example, each of the intelligent headwear PPE device 200, the intelligent hand wear PPE device 220, the intelligent footwear PPE device 240, the intelligent eyewear PPE device 260 may communicate their respective sets of safety data 130 to the intelligent clothing PPE device 270 (e.g., via Bluetooth wireless communication), and the intelligent clothing PPE device 270 may communicate its set of safety data 130, along with the sets of safety data 130 received from the other PPE devices 106, to the ICSS 102 (e.g., via a WiFi connection to the network 108).

In some embodiments, the ICSS 102 includes various plant operation systems distributed throughout the industrial plant 100. For example, referring again to FIG. 1, the ICSS 102 may include a control room system 150, a superintendent system 152, a safety team system 154, a managerial system 156, and an employee system 158.

In some embodiments, the control room system 150 includes a system for monitoring and controlling operational aspects of the industrial plant 100. For example, the control room system may include systems for monitoring and controlling operation of plant devices 104. In some embodiments, the control system 150 includes one or more control room terminals. A control room terminal may include a computer system similar to that of the computer system 1000 described with regard to at least FIG. 6.

In some embodiments, the superintendent system 152 includes a system for interacting with a superintendent that is tasked with overseeing operation of the industrial plant 100. For example, the superintendent system 152 may include a system for reporting the operational and safety status of the industrial plant 100 to the superintendent. In some embodiments, the superintendent system 152 includes a superintendent computer terminal that is accessible by the superintendent to review the information regarding the operational and safety status of the industrial plant 100. The superintendent computer terminal may include a computer system similar to that of the computer system 1000 described with regard to at least FIG. 6.

In some embodiments, the safety team system 154 includes a system for interacting with safety personnel of a safety team tasked with overseeing safety of the industrial plant 100. For example, the safety team system 154 may include a system for reporting the operational and safety status of the industrial plant 100 to some or all of the persons of the safety team. In some embodiments, the safety team system 154 includes one more safety team computer terminals that are accessible by the personnel of a safety team to review the information regarding the operational and safety status of the industrial plant 100. A safety team computer terminal may include a computer system similar to that of the computer system 1000 described with regard to at least FIG. 6.

In some embodiments, the managerial system 156 includes a system for interacting with managing personnel of tasked with overseeing performance of the employees of the industrial plant 100. For example, the managerial system 156 may include a system for reporting to each manager of the industrial plant 100, performance and safety data for the subset of employees managed by the manger. In some embodiments, the managerial system 156 includes, for each manager, a manager computer terminal that is accessible by the manger to review performance and safety data for the subset of employees managed by the manger. A manager computer terminal may include a computer system similar to that of the computer system 1000 described with regard to at least FIG. 6.

In some embodiments, the employee system 158 includes a system for interacting with employees of the industrial plant 100 (e.g., one or more of the persons 110 working in the industrial plant 100). For example, the employee system 158 may include a system for reporting, to the employees, performance and safety data for the employees. In some embodiments, the employee system 158 includes, for individual employees, an employee computer terminal that is accessible by the employee to review performance and safety data for the employee. An employee computer terminal may include a computer system similar to that of the computer system 1000 described with regard to at least FIG. 6. In some embodiments, an employee system 158 for an employee may be integrated into an intelligent PPE system 105 worn by the employee. For example, the employee system 158 may include a head-up display integrated into the intelligent eyewear 260, to display safety information for the employee on a lens of the eyewear 260 such that it is viewable by the employee while engaging in work duties. As a further example, the employee system 158 may include a speaker integrated into the intelligent headwear 221, to audibly convey safety information for the employee such that it can be heard by the employee while engaging in work duties.

In some embodiments, the ISS 122 monitors safety data 130 received from intelligent PPE devices 106, process the safety data to assess the safety status of the industrial plant 100 to identify any potential and actual safety incidents, and, if potential or actual safety issues are identified, alerts one or more entities of the ICSS 102 to the potential and/or actual safety issues and/or takes action to alleviate the potential and/or actual safety issues. For example, if the ISS 122 identifies relatively minor safety incidents for a person 110 that have occurred less than a threshold number of times, the ISS 122 may provide, to the person 110, an alert indicative of the relatively minor safety incidents; however, if the ISS 122 identifies relatively minor safety incidents that have occurred more than the threshold number of times, the ISS 122 may provide, to the person and other entities of the ICSS 102 (e.g., the control room system, the superintendent, a safety team, and/or the person's manager) an alert indicative of the relatively minor safety incidents. In some embodiments, if the ISS 122 identifies the occurrence of a critical safety incident, the ISS 122 may initiate responsive actions, such as ceasing certain operations of the industrial plant 100 and/or alerting the entities of the ICSS 102 (e.g., including the person, the control room system, the superintendent, a safety team, and/or the person's manager).

Figure 5:
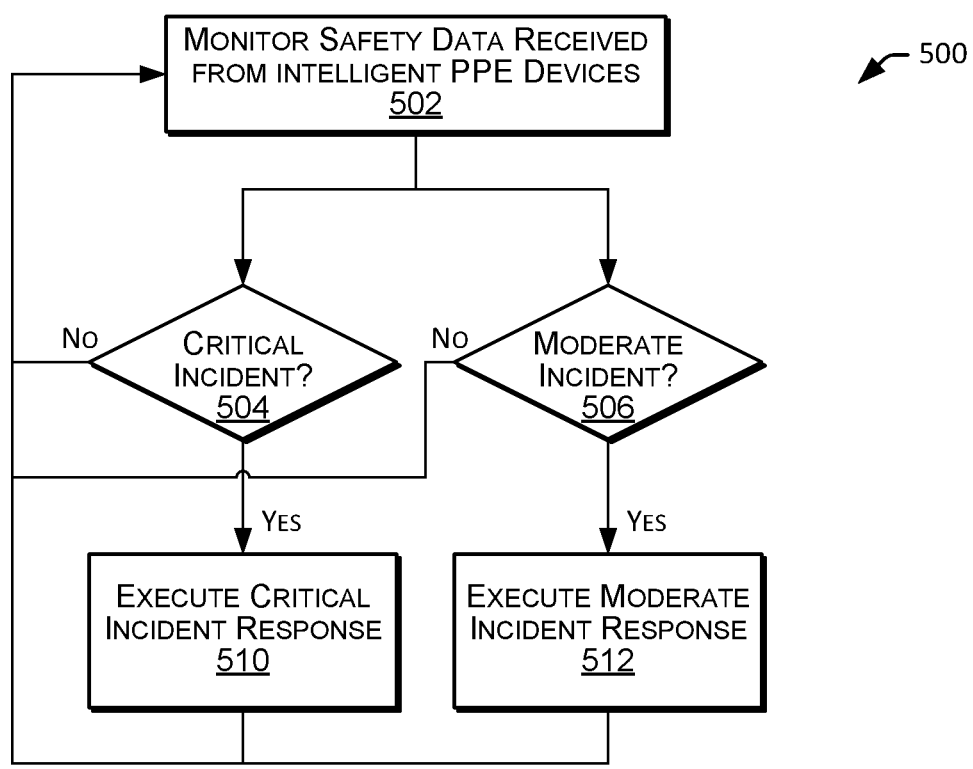
FIG. 5 is a flowchart that illustrates a method of operating an industrial plant integrated control and safety system (ICSS) in accordance with one or more embodiments.

FIG. 5 is a flowchart that illustrates a method 500 of operating an industrial plant integrated control and safety system (ICSS) in accordance with one or more embodiments. Method 500 can include monitoring safety data received from PPE devices (block 502). In some embodiments, monitoring safety data received from PPE devices includes the ISS 122 receiving the safety data 130 communicated to the ICSS 102 from one or more intelligent PPE devices 106 of one or more intelligent PPE systems 105, each worn by a person 110 located in the industrial plant 100. For example, referring to the example embodiment of the intelligent PPE system 105 of FIG. 4, monitoring safety data 130 received from PPE devices 106 may include the ISS 122 receiving the sets of safety data 130 generated by each of the intelligent headwear PPE device 200, the intelligent hand wear PPE device 220, the intelligent footwear PPE device 240, the intelligent eyewear PPE device 260, and the intelligent clothing PPE device 270.

The method 500 can include determining whether a critical (or "red flag") safety incident or moderate (or "yellow flag") safety incident has occurred (blocks 504 and 506, respectively). In some embodiments, determining whether a safety incident has occurred includes the ISS 122 assessing the received safety data 130 to determine whether a safety incident has occurred at the industrial plant 100. The method 500 can include, in response to determining that no safety incident has occurred (or "white flag" conditions), continuing to monitor the safety data received from PPE devices (block 502). The method 500 can include, in response to determining that a safety incident has occurred, executing a corresponding response (blocks 510 and 512).

In some embodiments determining whether a critical or moderate or minor safety incident has occurred includes the ISS 122 assessing the nature and/or frequency of a safety incident. A critical incident may be defined, for example, as a monitored condition being elevated above a threshold or elevated above 80% of the threshold for a given duration of time. Thus for example, if a heart rate threshold is set at 200 beats per minute and a duration is set to 10 minutes, then the ISS 122 may identify a safety incident as a critical safety incident in response to determining that the safety data 130 indicates that a person 110 has a heart rate above the threshold heart rate of 200 beats per minute or that the person 110 has a heart rate above 160 beats per minute for at least 10 minutes. The method 500 can include, in response to determining that a critical safety incident has occurred, executing a critical incident response (block 510). This can include, for example, ceasing certain operations of the industrial plant 100 and/or alerting the entities of the ICSS 102 (e.g., including the person, the control room system, the superintendent, a safety team, and/or the person's manager). For example, if the ISS 122 determines that one or more employees are experiencing a health crisis in a portion of the industrial plant 100, such as one or more persons 110 experiencing a heart rate above the threshold heart rate of 200 beats per minute, the ISS 122 may initiate suspension of plant operations in that portion of the industrial plant 100, send a corresponding alert to the control room terminals of the control room system 150, send a corresponding alert to the superintendent computer terminal of the superintendent system 152 for presentation to the superintendent that is tasked with overseeing operation of the industrial plant 100, send a corresponding alert to the safety team computer terminals of the safety team system 154 for presentation to personnel of the safety team tasked with overseeing safety of the industrial plant 100, and/or send a corresponding alert to a manager computer terminal of the managerial system 156 associated with the manager for the person 110 for presentation to the manager of the person 110.

A moderate incident may be defined as a monitored condition being elevated above 50% of a threshold for a given duration of time. Thus for example, if a heart rate threshold is set at 200 beats per minute and a duration is set to 10 minutes, then the ISS 122 may identify a moderate safety incident in response to determining that the safety data 130 indicates that a person 110 has a heart rate heart rate above 100 beats per minute for at least 10 minutes. The method 500 can include, in response to determining that a moderate safety incident has occurred, executing a moderate incident response (block 512). This can include, for example, alerting certain entities of the ICSS 102. For example, if the ISS 122 determines that a person 110 is experiencing a moderate health issue, such as the person 110 experiencing a heart rate heart rate above 100 beats per minute for at least 10 minutes, the ISS 122 may send a corresponding alert to the control room terminals of the control room system 150, and send a corresponding alert to the person 110 (e.g., via the intelligent PPE system 105 worn by a person 110 and/or an employee computer terminal associated with the person 110).

Figure 6:
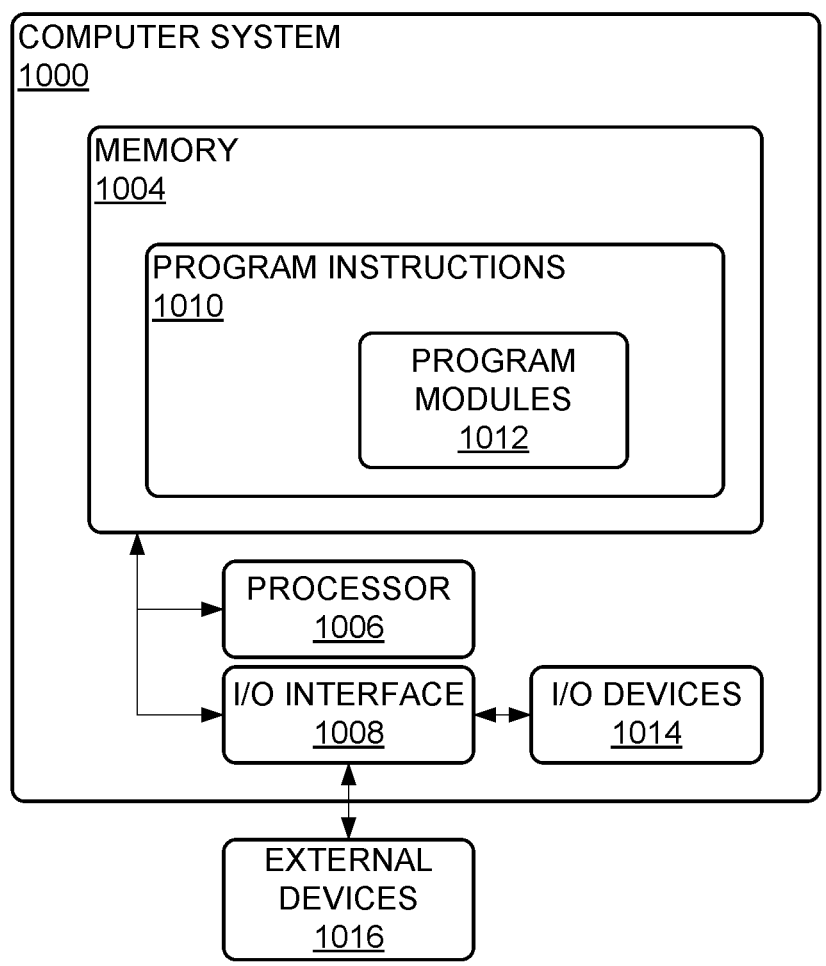
FIG. 6 is a diagram that illustrates an example computer system in accordance with one or more embodiments.

FIG. 6 is a diagram that illustrates an example computer system (or "system") 1000 in accordance with one or more embodiments. The system 1000 may include a memory 1004, a processor 1006 and an input/output (I/O) interface 1008. The memory 1004 may include one or more of non-volatile memory (for example, flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), and bulk storage memory (for example, CD-ROM or DVD-ROM, hard drives). The memory 1004 may include a non-transitory computer-readable storage medium having program instructions 1010 stored thereon. The program instructions 1010 may include program modules 1012 that are executable by a computer processor (for example, the processor 1006) to cause the functional operations described, such as those described with regard to the ICSS 102, the PCS 120, the ISS 122, and/or the intelligent PPS system 105.

The processor 1006 may be any suitable processor capable of executing program instructions. The processor 1006 may include a central processing unit (CPU) that carries out program instructions (e.g., the program instructions of the program module(s) 1012) to perform the arithmetical, logical, and input/output operations described. The processor 1006 may include one or more processors. The I/O interface 1008 may provide an interface for communication with one or more I/O devices 1014, such as sensors, a computer mouse, a keyboard, speakers and a display screen (e.g., an electronic display for displaying a graphical user interface (GUI)). The I/O devices 1014 may be connected to the I/O interface 1008 via a wired connection (e.g., Industrial Ethernet connection) or a wireless connection (e.g., a Wi-Fi connection). The I/O interface 1008 may provide an interface for communication with one or more external devices 1016, such as other computers and networks. In some embodiments, the I/O interface 1008 includes one or both of an antenna and a transceiver. In some embodiments, the external devices 1016 include one or more of network 108, plant devices 104, intelligent PPE device systems 105, intelligent PPE devices 106, the ICSS 102, the PCS 120, the ISS 122 and/or the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (for example, via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. An industrial plant system, comprising:
   an industrial safety system (ISS) configured to monitor a safety status of an industrial plant; and
   one or more intelligent personal protective equipment (PPE) systems configured to be worn by personnel located in the industrial plant, wherein each of the intelligent PPE systems comprises one or more intelligent PPE devices configured to sense personal and environmental characteristics of a person wearing the intelligent PPE system, and wherein each of the intelligent PPE systems is configured to transmit, to the industrial safety system, safety data corresponding to the personal and environmental characteristics of the person wearing the intelligent PPE system, sensed by the one or more intelligent PPE devices of the intelligent PPE system, and wherein the ISS is configured to:
collect, from the one or more intelligent PPE systems, the safety data;
determine, based on the safety data collected, whether a critical safety incident or a moderate safety incident has occurred, wherein determining that a critical safety incident has occurred comprises determining that a monitored condition of a person exceeds a critical threshold level for at least a given duration of time;
in response to determining that a moderate safety incident has occurred, send an alert to entities of the industrial plant system; and
in response to determining that a critical safety incident has occurred, suspend operations of the industrial plant and send an alert to entities of the industrial plant system, wherein suspending operations of the industrial plant comprises:
determining, based on the safety data collected, a portion of the industrial plant in which the person is located; and
suspending operations of the portion of the industrial plant determined.

2. The system of claim 1, wherein the one or more intelligent PPE devices comprise one or more of the following: an intelligent headwear PPE device, an intelligent hand wear PPE device, an intelligent footwear PPE device, an intelligent eyewear PPE device, and an intelligent clothing device.

3. The system of claim 2, wherein the intelligent headwear PPE device comprises an intelligent safety helmet.

4. The system of claim 2, wherein the intelligent hand wear PPE device comprises intelligent safety gloves.

5. The system of claim 2, wherein the intelligent footwear PPE device comprises intelligent safety boots.

6. The system of claim 2, wherein the intelligent eyewear PPE device comprises intelligent safety glasses.

7. The system of claim 2, wherein the intelligent clothing PPE device comprises an intelligent safety belt.

8. The system of claim 1, further comprising a smart device coupled to a plant device, wherein the smart device is configured to transmit, to an intelligent PPE system worn by a person located in the industrial plant, environmental data indicative of a characteristic of the plant device, wherein the intelligent PPE system is configured to communicate the environmental data indicative of the characteristic of the plant device to the ISS, and wherein the safety data collected comprises the environmental data indicative of the characteristic of the plant device.

9. A method of operating an industrial plant, comprising:
sensing, by one or more intelligent personal protective equipment (PPE) systems worn by personnel located in an industrial plant, personal and environmental characteristics of the personnel, wherein each of the one or more intelligent PPE systems are worn by a person located in the industrial plant, wherein each of the intelligent PPE systems comprises one or more intelligent PPE devices sensing personal and environmental characteristics of the person wearing the intelligent PPE system, and wherein the personal and environmental characteristics of the personnel comprise the personal and environmental characteristics sensed by the one or more intelligent PPE devices of the one or more intelligent PPE systems;
transmitting, by the one or more PPE systems, safety data corresponding to the personal and environmental characteristics of the personnel; and
monitoring, by an industrial safety system (ISS), a safety status of the industrial plant, the monitoring comprising the ISS performing the following operations:
collecting, from the one or more intelligent PPE systems, the safety data;
determining, based on the safety data collected, that a moderate safety incident has occurred, wherein determining that a critical safety incident has occurred comprises determining that a monitored condition of a person exceeds a critical threshold level for at least a given duration of time; and
in response to determining that the moderate safety incident has occurred, sending an alert to entities of the industrial plant system
determining, based on the safety data collected, that a critical safety incident has occurred; and
in response to determining that the critical safety incident has occurred, suspending operations of the industrial plant and sending an alert to entities of the industrial plant system, wherein suspending operations of the industrial plant comprises:
determining a portion of the industrial plant in which the person is located; and
suspending operations of the portion of the industrial plant determined.

10. The method of claim 9, wherein the one or more intelligent PPE devices comprise one or more of the following: an intelligent headwear PPE device, an intelligent hand wear PPE device, an intelligent footwear PPE device, an intelligent eyewear PPE device, and an intelligent clothing device.

11. The method of claim 10, wherein the intelligent headwear PPE device comprises an intelligent safety helmet.

12. The method of claim 10, wherein the intelligent hand wear PPE device comprises intelligent safety gloves.

13. The method of claim 10, wherein the intelligent footwear PPE device comprises intelligent safety boots.

14. The method of claim 10, wherein the intelligent eyewear PPE device comprises intelligent safety glasses.

15. The method of claim 10, wherein the intelligent clothing PPE device comprises an intelligent safety belt.

16. The method of claim 9, further comprising an intelligent PPE system worn by a person located in the industrial plant receiving, from a smart device coupled to a plant device, environmental data indicative of a characteristic of the plant device, and the intelligent PPE system communicating the environmental data indicative of the characteristic of the plant device to the ISS, wherein the safety data collected comprises the environmental data indicative of the characteristic of the plant device.

17. A non-transitory computer readable medium comprising program instructions stored thereon that are executable by a processor to cause the following operations for operating an industrial plant:
sensing, by one or more intelligent personal protective equipment (PPE) systems worn by personnel located in an industrial plant, personal and environmental characteristics of the personnel, wherein each of the one or more intelligent PPE systems are worn by a person located in the industrial plant, wherein each of the intelligent PPE systems comprises one or more intelligent PPE devices sensing personal and environmental characteristics of the person wearing the intelligent PPE system, and wherein the personal and environmental characteristics of the personnel comprise the personal and environmental characteristics sensed by the one or more intelligent PPE devices of the one or more intelligent PPE systems;

transmitting, by the one or more PPE systems, safety data corresponding to the personal and environmental characteristics of the personnel; and monitoring, by an industrial safety system (ISS), a safety status of the industrial plant, the monitoring comprising the ISS performing the following operations:

collecting, from the one or more intelligent PPE systems, the safety data;

determining, based on the safety data collected, whether a critical safety incident or a moderate safety incident has occurred, wherein determining that a critical safety incident has occurred comprises determining that a monitored condition of a person exceeds a critical threshold level for at least a given duration of time; and in response to determining that a moderate safety incident has occurred, sending an alert to entities of the industrial plant system; and in response to determining that a critical safety incident has occurred, suspending operations of the industrial plant and sending an alert to entities of the industrial plant system, wherein suspending operations of the industrial plant comprises:

determining a portion of the industrial plant in which the person is located; and suspending operations of the portion of the industrial plant determined.

18. The system of claim 1, wherein the ISS is further configured to:

determine, based on the safety data collected, whether a personal safety incident for a person has occurred at least a threshold number of times, and in response to determining that the personal safety incident has occurred at least a threshold number of times, send an alert to the person indicating that the personal safety incident occurred.

19. The method of claim 9, further comprising:

determining, by the ISS based on the safety data collected, whether a personal safety incident for a person has occurred at least a threshold number of times, and in response to the ISS determining that the personal safety incident has occurred at least a threshold number of times, sending, by the ISS, an alert to the person indicating that the personal safety incident occurred.

20. The medium of claim 17, the monitoring further comprising:

determining, by the ISS based on the safety data collected, whether a personal safety incident for a person has occurred at least a threshold number of times, and in response to the ISS determining that the personal safety incident has occurred at least a threshold number of times, sending, by the ISS, an alert to the person indicating that the personal safety incident occurred.

\* \* \* \* \*